United States Patent
Kang et al.

(10) Patent No.: US 10,138,201 B2
(45) Date of Patent: Nov. 27, 2018

(54) COMPOUND FOR ORGANIC ELETROLUMINESCENT DEVICE AND ORGANIC ELECTROLUMINESCENT DEVICE INCLUDING THE SAME

(71) Applicant: SK CHEMICALS CO., LTD., Seongnam-si, Gyeonggi-Do (KR)

(72) Inventors: Ju-Sik Kang, Hwaseong-si (KR); Jeong Ho Park, Seongnam-si (KR); Suk Woon Jun, Suwon-si (KR); Yong-Jun Shin, Seoul (KR); Yu-Mi Chang, Gwangju-si (KR); Nam-Choul Yang, Seoul (KR); Jae-Kyun Park, Incheon (KR); Song Lee, Seoul (KR)

(73) Assignee: SK CHEMICALS CO., LTD., Seongnam-si (KR)

( * ) Notice: Subject to any disclaimer, the term of this patent is extended or adjusted under 35 U.S.C. 154(b) by 279 days.

(21) Appl. No.: 14/913,450

(22) PCT Filed: Jun. 17, 2014

(86) PCT No.: PCT/KR2014/005291
§ 371 (c)(1),
(2) Date: Feb. 22, 2016

(87) PCT Pub. No.: WO2015/026053
PCT Pub. Date: Feb. 26, 2015

(65) Prior Publication Data
US 2016/0204354 A1     Jul. 14, 2016

(30) Foreign Application Priority Data
Aug. 21, 2013   (KR) .................. 10-2013-0099148

(51) Int. Cl.
*H01L 51/00* (2006.01)
*C07C 211/54* (2006.01)
(Continued)

(52) U.S. Cl.
CPC .......... *C07C 211/54* (2013.01); *C07D 209/86* (2013.01); *C07D 307/91* (2013.01);
(Continued)

(58) Field of Classification Search
CPC ..... C07C 211/54; C07D 307/91; C09K 11/06; C09K 2211/1007; C09K 2211/1011;
(Continued)

(56) References Cited

U.S. PATENT DOCUMENTS

2014/0027747 A1   1/2014   Mun et al.

FOREIGN PATENT DOCUMENTS

| JP | 10-237438 A | 9/1998 |
| JP | 2000-247932 A | 9/2000 |

(Continued)

OTHER PUBLICATIONS

Office Action from Taiwan Intellectual Property Office, dated Dec. 22, 2017.

*Primary Examiner* — Ruiyun Zhang
(74) *Attorney, Agent, or Firm* — STIP Law Group, LLC

(57) ABSTRACT

This invention relates to a compound for an organic electroluminescent device and to an organic electroluminescent device including the same. This compound for an organic electroluminescent device has high thermal stability, high triplet energy and high hole transport capability, and the organic electroluminescent device including the same is improved in thermal stability and light emission efficiency. When this compound is used as a hole transport layer material, a triplet exciton of a phosphorescent light emitting material is confined, thus improving efficiency of the organic electroluminescent device.

8 Claims, 1 Drawing Sheet

(51) Int. Cl.
*C07D 209/86* (2006.01)
*C07D 307/91* (2006.01)
*C09K 11/06* (2006.01)
*H01L 51/50* (2006.01)

(52) U.S. Cl.
CPC .......... *C09K 11/06* (2013.01); *H01L 51/0059* (2013.01); *H01L 51/0061* (2013.01); *H01L 51/0072* (2013.01); *H01L 51/0073* (2013.01); *C07C 2603/18* (2017.05); *C09K 2211/1007* (2013.01); *C09K 2211/1011* (2013.01); *C09K 2211/1029* (2013.01); *C09K 2211/1088* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC .... C09K 2211/1029; C09K 2211/1088; H01L 51/0059; H01L 51/0061; H01L 51/0072; H01L 51/0073; H01L 51/5012
USPC .................... 428/690, 917; 257/40, E27.119, 257/E51.026; 548/440; 549/460
See application file for complete search history.

(56) References Cited

FOREIGN PATENT DOCUMENTS

| | | | |
|---|---|---|---|
| JP | 2009-016718 A | | 1/2009 |
| JP | 2009016718 A | * | 1/2009 |
| TW | 201247840 A | | 12/2012 |
| WO | WO2012-134203 A2 | | 10/2012 |

* cited by examiner

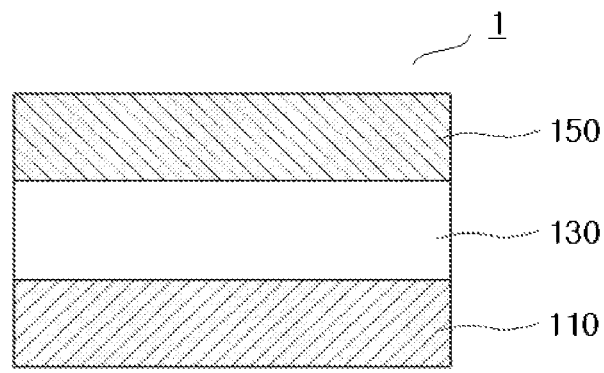
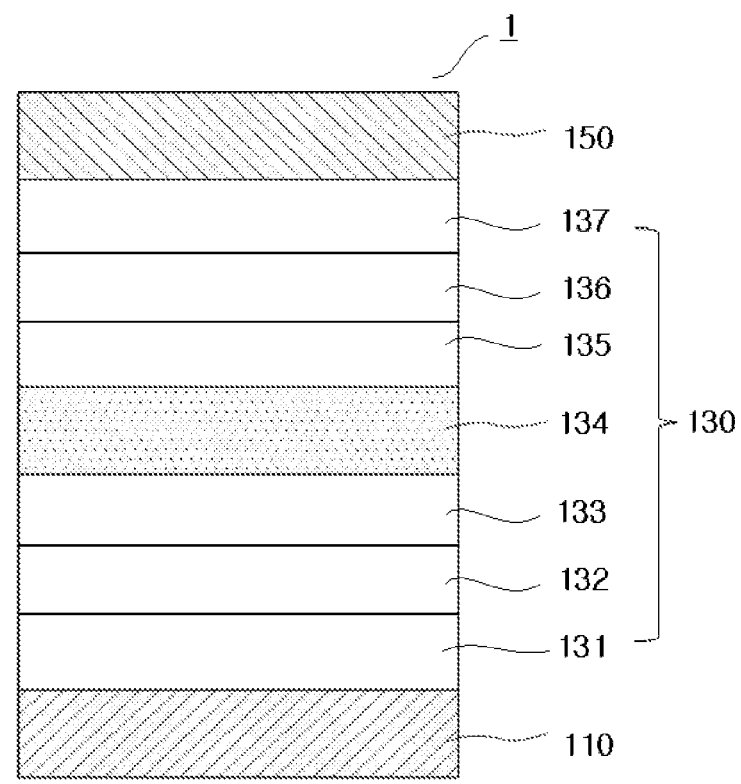

COMPOUND FOR ORGANIC ELETROLUMINESCENT DEVICE AND ORGANIC ELECTROLUMINESCENT DEVICE INCLUDING THE SAME

This is a U.S. national stage application of PCT Application No. PCT/KR2014/005291 under 35 U.S.C. 371, filed Jun. 17, 2014 in English, claiming the priority benefit of Korean Application No. 10-2013-0099148, filed Aug. 21, 2013, which is hereby incorporated by reference.

TECHNICAL FIELD

The present invention relates to a compound for an organic electroluminescent device and an organic electroluminescent device including the same, and more particularly, to an amine-based compound for an organic electroluminescent device, having a heterocyclic structure, and to an organic electroluminescent device including the same.

BACKGROUND ART

Organic electroluminescent (EL) devices have a simpler structure, various processing advantages, higher brightness, superior viewing angle properties, quicker response rate, and a lower driving voltage compared to other flat panel displays such as liquid crystal displays (LCDs), plasma display panels (PDPs), field emission displays (FEDs), etc., and are thus being thoroughly developed so as to be utilized as light sources of flat panel displays such as wall-mountable TVs, etc. or backlight units of the displays, illuminators, advertisement boards and so on.

Typically, when a direct-current voltage is applied to an organic EL device, holes injected from an anode and electrons injected from a cathode recombine to form electron-hole pairs, namely, excitons. While the excitons return to a stable ground state, energy corresponding thereto is transferred to a light emitting material and is thereby converted into light.

In order to increase efficiency and stability of an organic EL device, since C. W. Tang et al. of Eastman Kodak Company made an organic EL device operating at low voltage by forming a tandem organic thin film between two opposite electrodes (C. W. Tang, S. A. Vanslyke, Applied Physics Letters, vol. 51, pp. 913, 1987), extensive and intensive research into organic materials for organic EL devices having a multilayered thin-film structure has been ongoing. The efficiency and lifetime of such a tandem organic EL device are closely related to the molecular structure of a material for the thin film. For example, quantum efficiency may greatly vary depending on the structure of the material for the thin film, particularly a host material, a hole transport layer material or an electron transport layer material. When thermal stability of the material decreases, the material may be crystallized at a high temperature or a driving temperature, undesirably shortening the lifetime of the device.

Hole transport materials for use in organic EL devices, which have been known to date, are problematic because thin films formed therefrom using vacuum deposition are thermally and electrically unstable, and thus may rapidly crystallize due to heat generated upon device driving and also the film materials may change, undesirably deteriorating the light emission efficiency of the devices. Further, non-emission parts referred to as dark spots may increasingly occur, and the voltage may increase upon constant-current driving, undesirably damaging the devices.

Also, organic EL devices using a phosphorescent light emitting material do not confine a triplet exciton produced in the light emitting material of a light emitting layer due to low triplet energy, undesirably lowering the light emission efficiency of the devices.

DISCLOSURE

Technical Problem

Accordingly, an object of the present invention is to provide a compound for an organic EL device, which may have high thermal stability, high triplet energy and high hole transport capability.

Another object of the present invention is to provide an organic EL device, which includes the compound as above and is thus improved in thermal stability and light emission efficiency, and in which the above compound is used as a hole transport layer material, thereby confining a triplet exciton of a phosphorescent light emitting material, ultimately improving efficiency of the organic EL device.

Technical Solution

In order to accomplish the above objects, an aspect of the present invention provides a compound for an organic EL device, as represented by Chemical Formula 1 below.

[Chemical Formula 1]

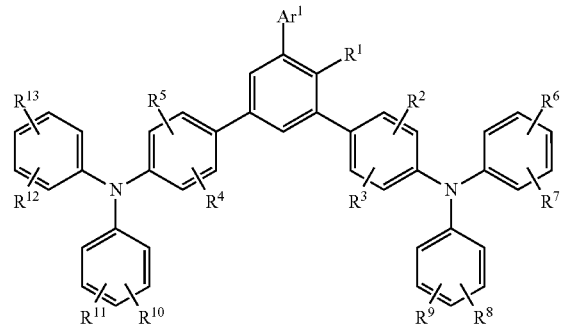

In Chemical Formula 1, $Ar^1$ is a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or $Ar^1$ is further coupled with a carbon atom adjacent to a carbon atom linked therewith to form a substituted or unsubstituted fused C3 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, $R^1$ is a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or $R^1$ is coupled with $Ar^1$ to form a substituted or unsubstituted fused C1 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, and $R^2$ to $R^{13}$ are identical to or different from each other, and $R^2$ to $R^{13}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or at least one of $R^2$ to $R^{13}$ is further coupled with a carbon atom adjacent to a carbon atom linked therewith to form a substituted or unsubstituted fused C3 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group.

According to a preferred embodiment of the present invention, the compound for an organic EL device is represented by Chemical Formula 2 below.

[Chemical Formula 2]

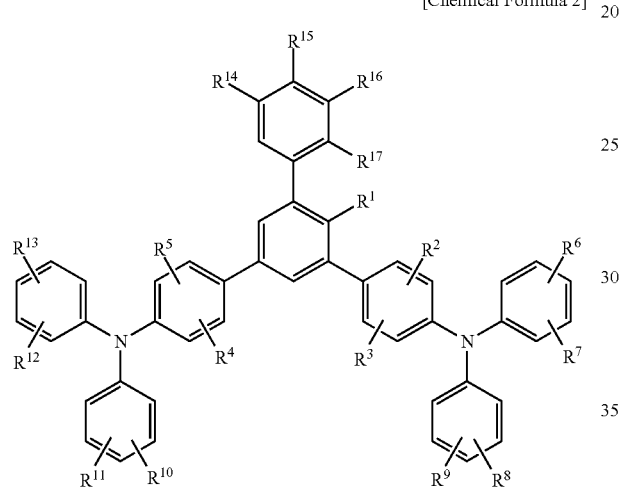

In Chemical Formula 2, $R^2$ to $R^{16}$ are identical to or different from each other, and $R^2$ to $R^{16}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or at least one of $R^2$ to $R^{16}$ is further coupled with a carbon atom adjacent to a carbon atom linked therewith to form a substituted or unsubstituted fused C3 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, and $R^1$ and $R^{17}$ are identical to or different from each other, and $R^1$ and $R^{17}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or $R^1$ and $R^{17}$, respectively, are linked to form a substituted or unsubstituted fused C1 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, together with 4 carbons atom therebetween.

According to a preferred embodiment of the present invention, the compound for an organic EL device is represented by any one selected from among Chemical Formulas 3 to 6 below.

[Chemical Formula 3]

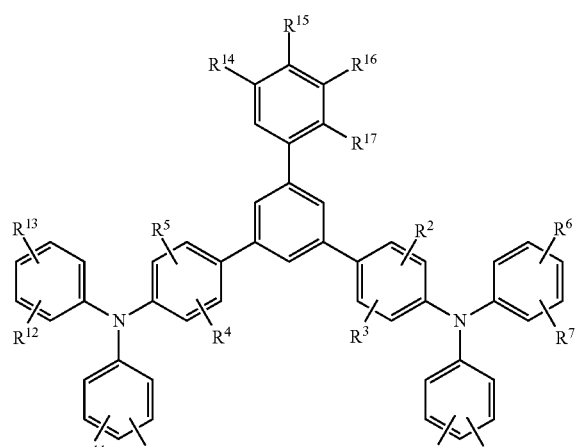

[Chemical Formula 4]

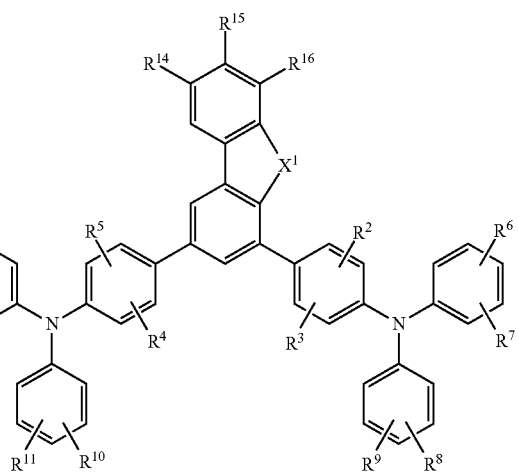

[Chemical Formula 5]

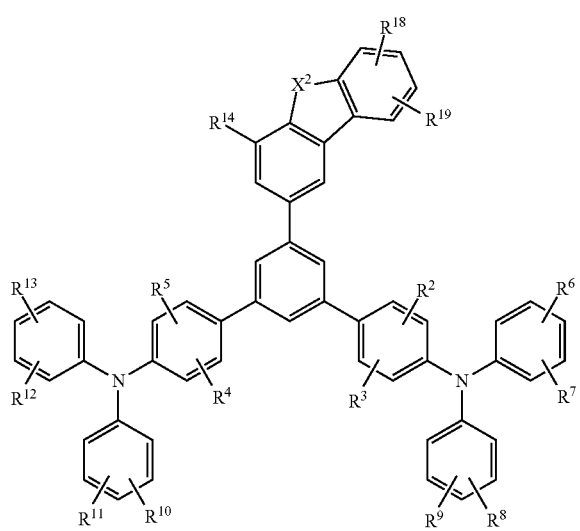

-continued

[Chemical Formula 6]

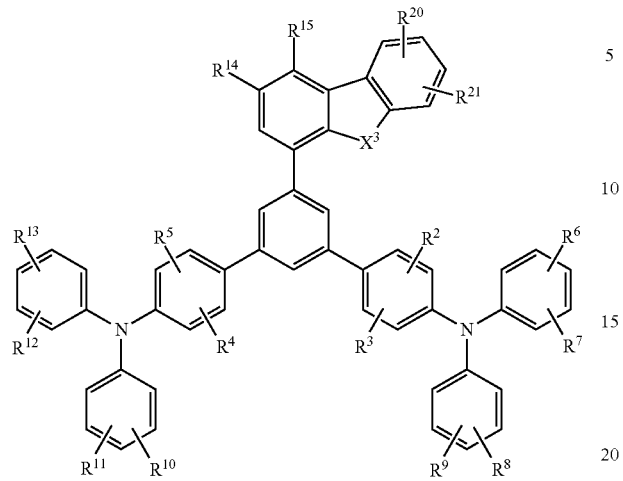

In Chemical Formula 3 to 6, $X^1$ to $X^3$ are identical to or different from each other, and $X^1$ to $X^3$ are each independently an oxygen atom, a sulfur atom,

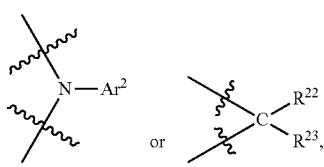

$Ar^2$ is a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, $R^{22}$ and $R^{23}$ are identical to or different from each other, and $R^{22}$ and $R^{23}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, $R^2$ to $R^{13}$ are identical to or different from each other, and $R^2$ to $R^{13}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or at least one of $R^2$ to $R^{13}$ is further coupled with a carbon atom adjacent to a carbon atom linked therewith to form a substituted or unsubstituted fused C3 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, and $R^{14}$ to $R^{16}$, and $R^{18}$ to $R^{21}$ are identical to or different from each other, and $R^{14}$ to $R^{16}$, and $R^{18}$ to $R^{21}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group.

According to a preferred embodiment of the present invention, $X^1$ is

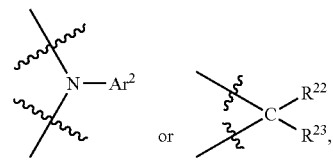

$Ar^2$ is a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, and $R^{22}$ and $R^{23}$ are identical to or different from each other, and $R^{22}$ and $R^{23}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group.

According to a preferred embodiment of the present invention, $X^2$ and $X^3$ are identical to or different from each other, and $X^2$ and $X^3$ are each independently an oxygen atom or

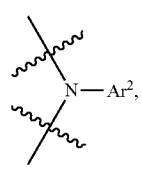

and $Ar^2$ is a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group.

According to a preferred embodiment of the present invention, $R^{14}$ to $R^{16}$ are identical to or different from each other, and $R^{14}$ to $R^{16}$ are each independently a hydrogen atom,

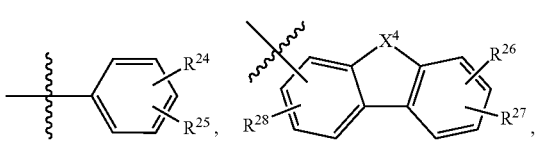

a substituted or unsubstituted C1 to C30 alkyl group, a substituted or unsubstituted C3 to C30 cycloalkyl group, or a substituted or unsubstituted C1 to C30 heterocycloalkyl group, $X^4$ is an oxygen atom, a sulfur atom,

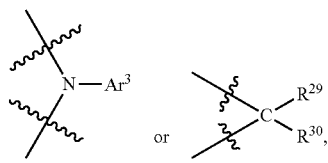

$Ar^3$ is a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, $R^{29}$ and $R^{30}$ are identical to or different from each other, and $R^{29}$ and $R^{30}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, and $R^{24}$ to $R^{28}$ are identical to or different from each other, and $R^{24}$ to $R^{28}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group.

According to a preferred embodiment of the present invention, $R^2$ to $R^{13}$ are identical to or different from each other, and $R^2$ to $R^{13}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group.

According to a preferred embodiment of the present invention, $R^2$ to $R^{13}$ are identical to or different from each other, and $R^2$ to $R^{13}$ are each independently a hydrogen atom,

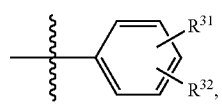

a substituted or unsubstituted C1 to C30 alkyl group, a substituted or unsubstituted C3 to C30 cycloalkyl group, or a substituted or unsubstituted C1 to C30 heterocycloalkyl group, and $R^{31}$ and $R^{32}$ are identical to or different from each other, and $R^{31}$ and $R^{32}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group.

Examples of the substituted or unsubstituted C6 to C30 aryl group may include a substituted or unsubstituted phenyl group, a substituted or unsubstituted biphenyl group, a substituted or unsubstituted terphenyl group, a substituted or unsubstituted naphthalenyl group, a substituted or unsubstituted anthracenyl group, a substituted or unsubstituted phenanthrenyl group, a substituted or unsubstituted fluorenyl group, a substituted or unsubstituted spirofluorenyl group, a substituted or unsubstituted pyrenyl group, or a substituted or unsubstituted perylenyl group.

Examples of the substituted or unsubstituted C1 to C30 heteroaryl group may include a substituted or unsubstituted pyridinyl group, a substituted or unsubstituted pyrimidinyl group, a substituted or unsubstituted triazinyl group, a substituted or unsubstituted thiophenyl group, a substituted or unsubstituted pyrrolyl group, a substituted or unsubstituted benzothiophenyl group, a substituted or unsubstituted indolyl group, a substituted or unsubstituted imidazo[1,2-a]pyridinyl group, a substituted or unsubstituted benzimidazolyl group, a substituted or unsubstituted indazolyl group, a substituted or unsubstituted phenothiazinyl group, a substituted or unsubstituted phenazinyl group, a substituted or unsubstituted carbazolyl group, a substituted or unsubstituted dibenzothiophenyl group, a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzotriazolyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, or a substituted or unsubstituted phenanthrolinyl group. Preferably useful is a substituted or unsubstituted pyridinyl group, a substituted or unsubstituted pyrimidinyl group, a substituted or unsubstituted triazinyl group, a substituted or unsubstituted thiophenyl group, a substituted or unsubstituted pyrrolyl group, a substituted or unsubstituted benzothiophenyl group, a substituted or unsubstituted indolyl group, a substituted or unsubstituted imidazo[1,2-a]pyridinyl group, a substituted or unsubstituted benzimidazolyl group, a substituted or unsubstituted indazolyl group, a substituted or unsubstituted phenothiazinyl group, a substituted or unsubstituted phenazinyl group, a substituted or unsubstituted carbazolyl group, or a substituted or unsubstituted dibenzothiophenyl group.

According to a preferred embodiment of the present invention, the compound for an organic EL device is any one elected from among compounds 1 to 31 represented by the following chemical formulas.

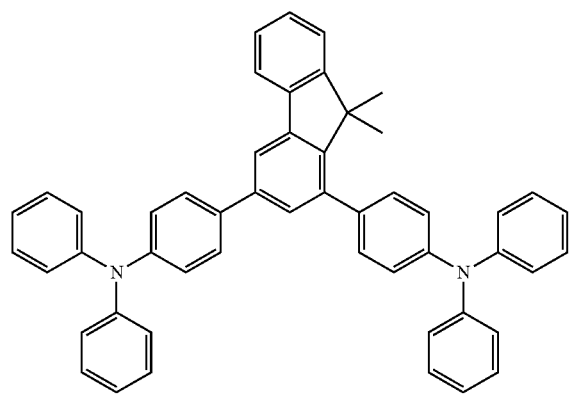
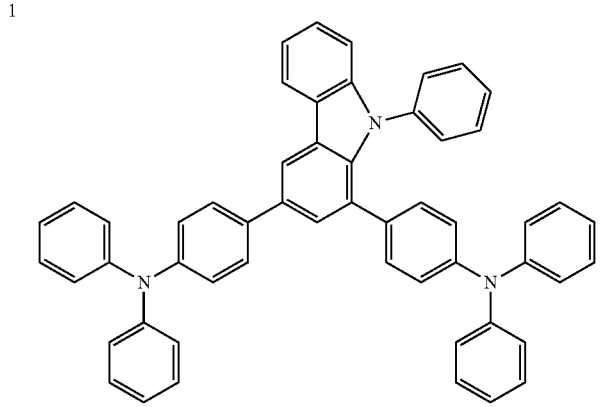
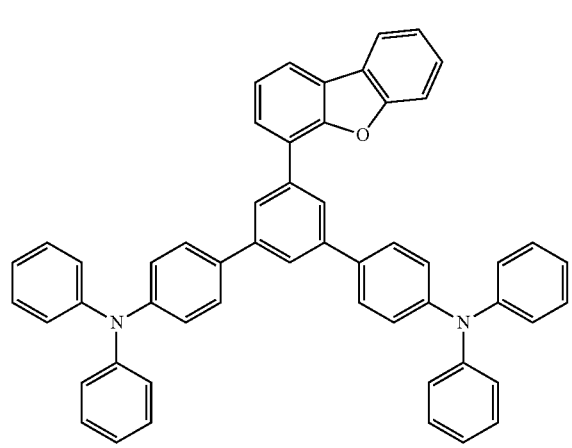
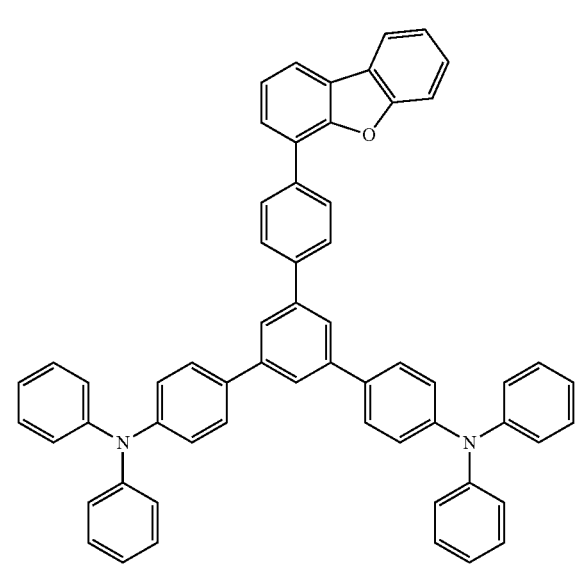
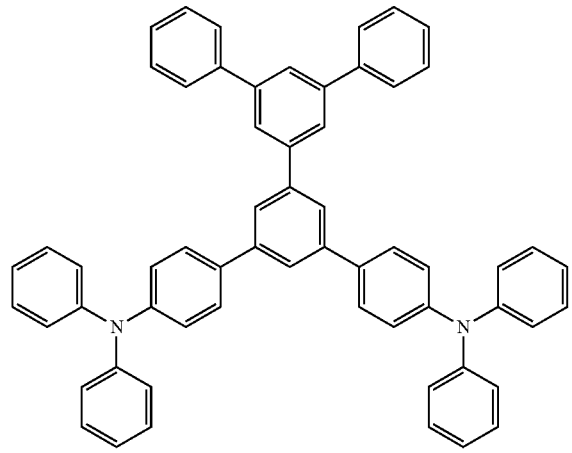
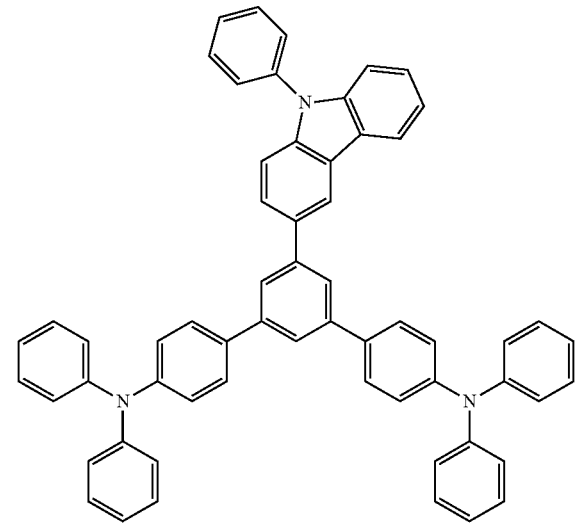

-continued
7
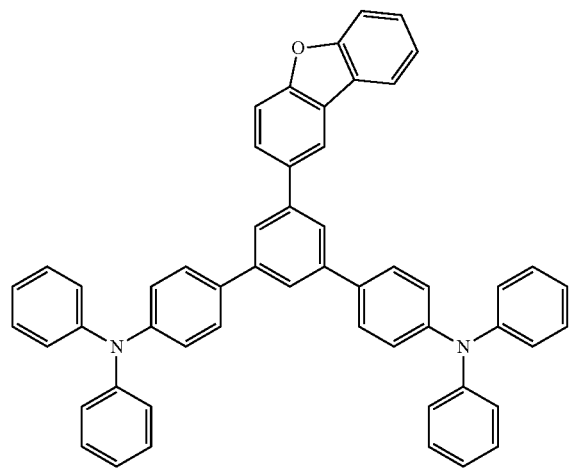
8
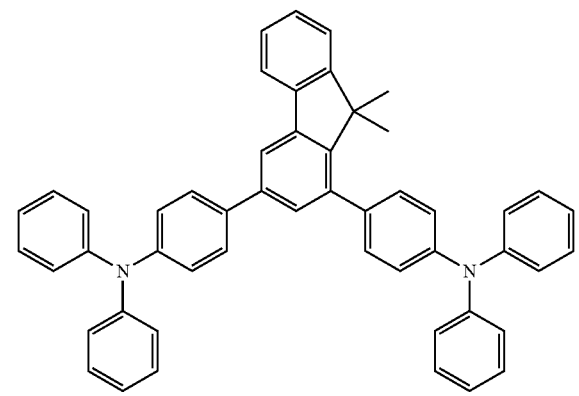
9 10
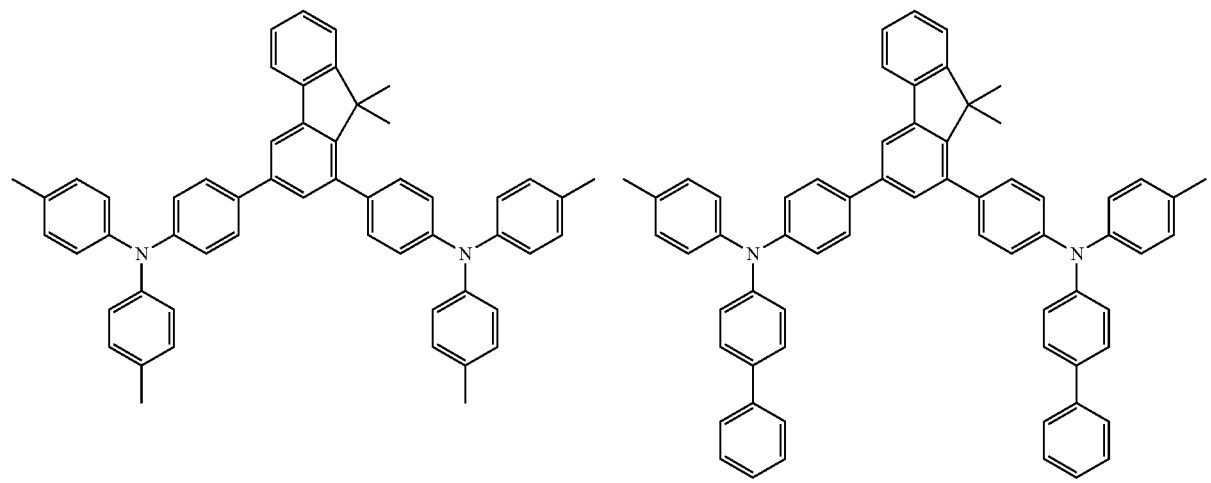
11
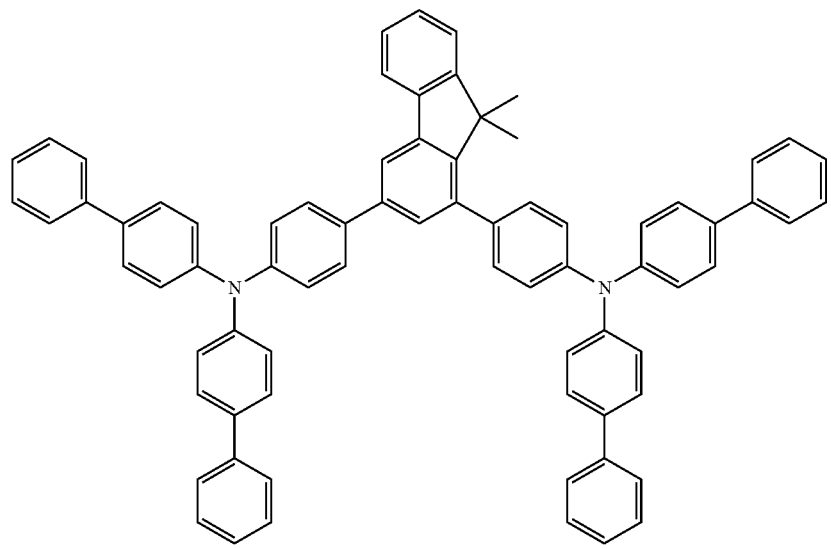

12
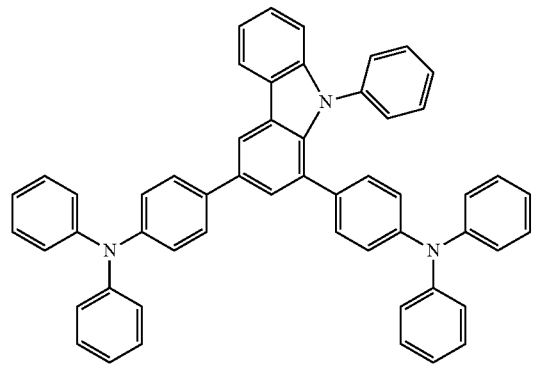
13
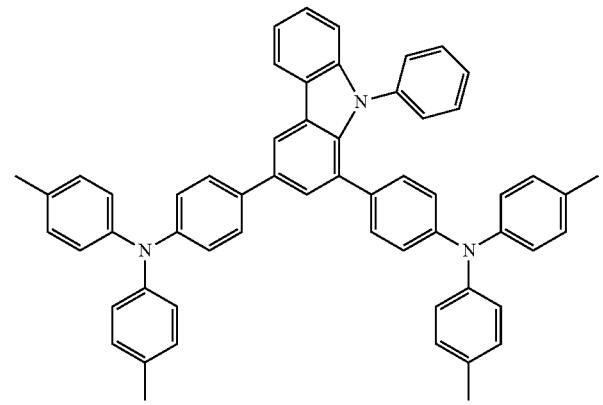
14
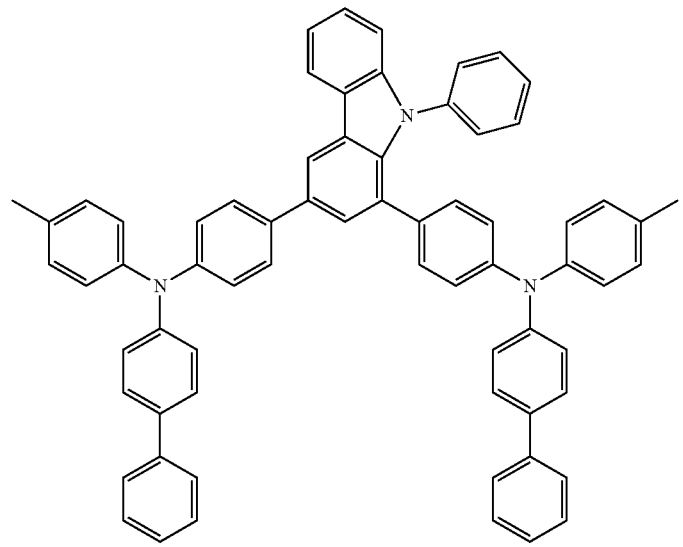
15
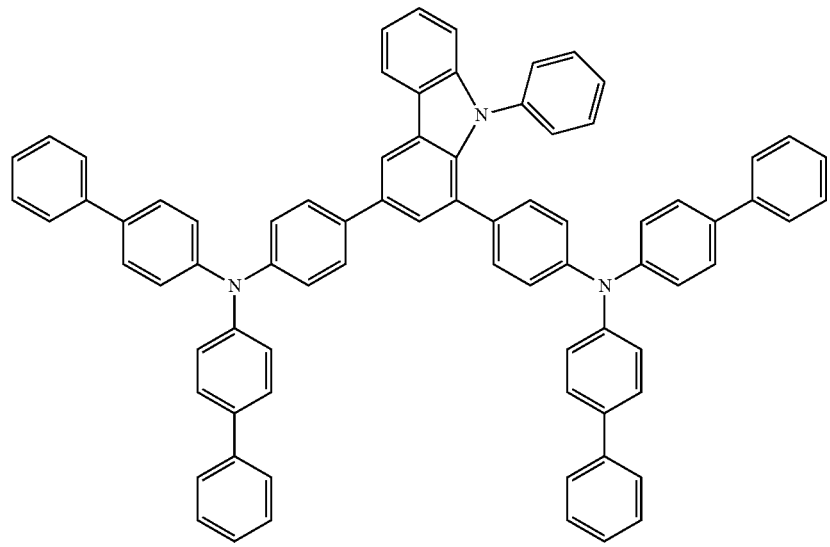

-continued
16
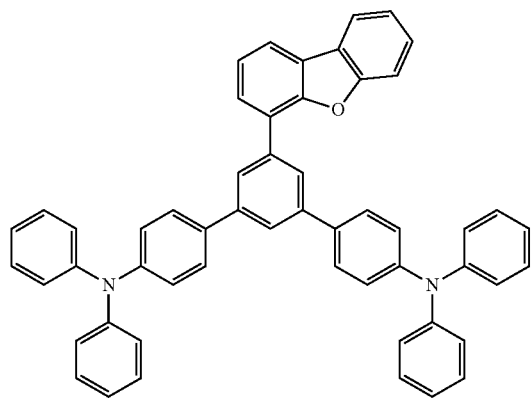
17
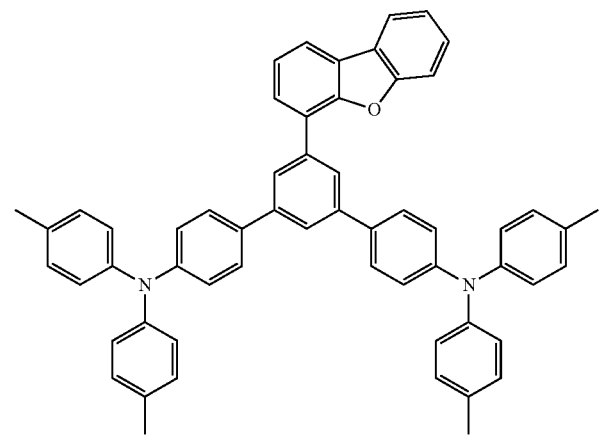
18
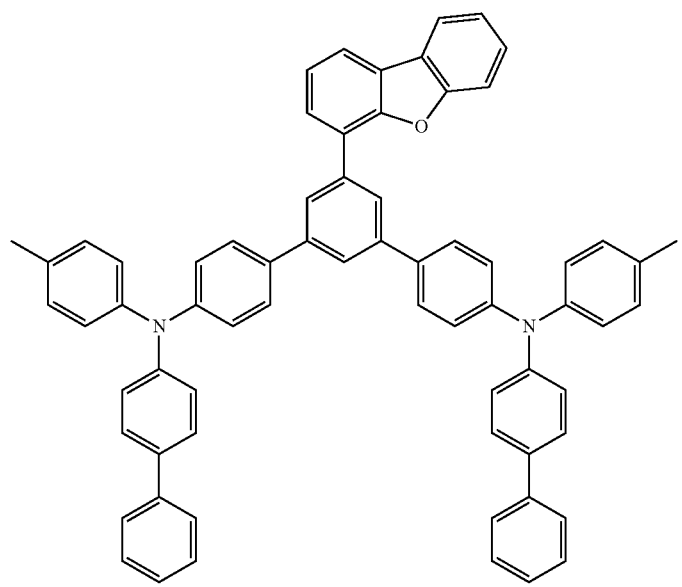
19
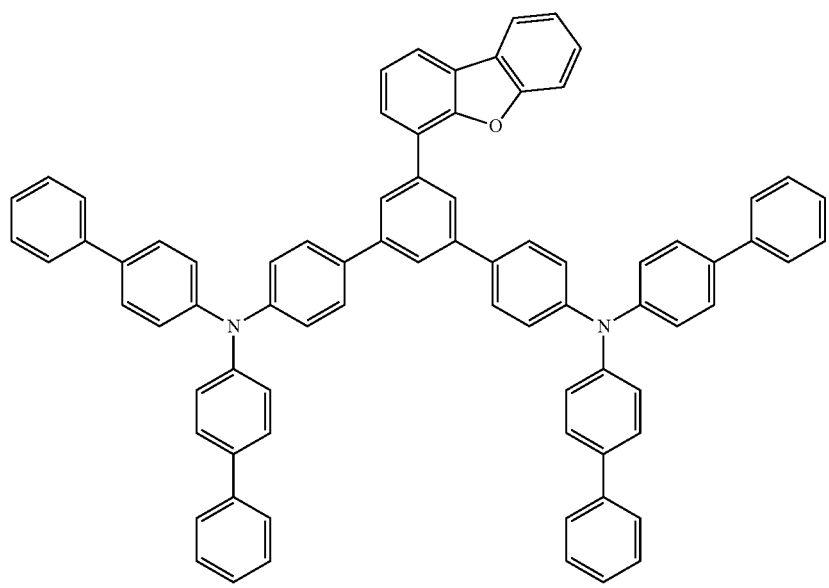

20
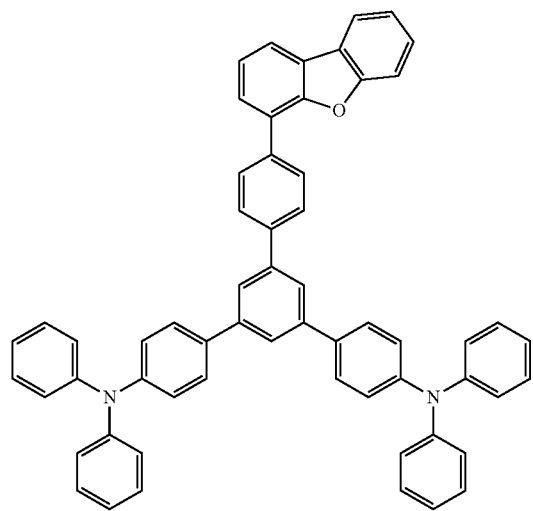
21
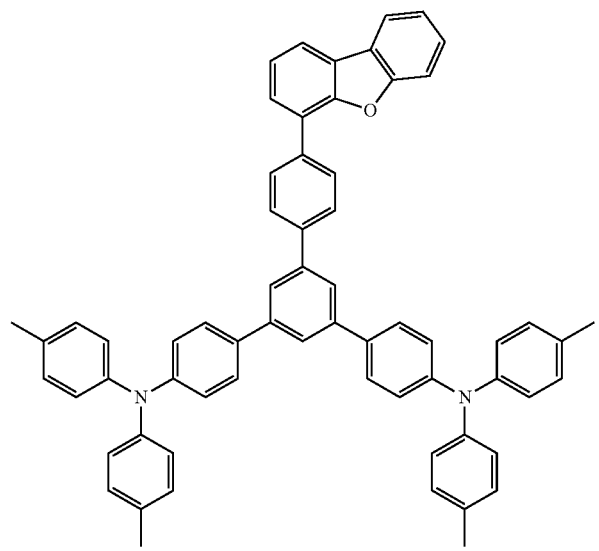
22
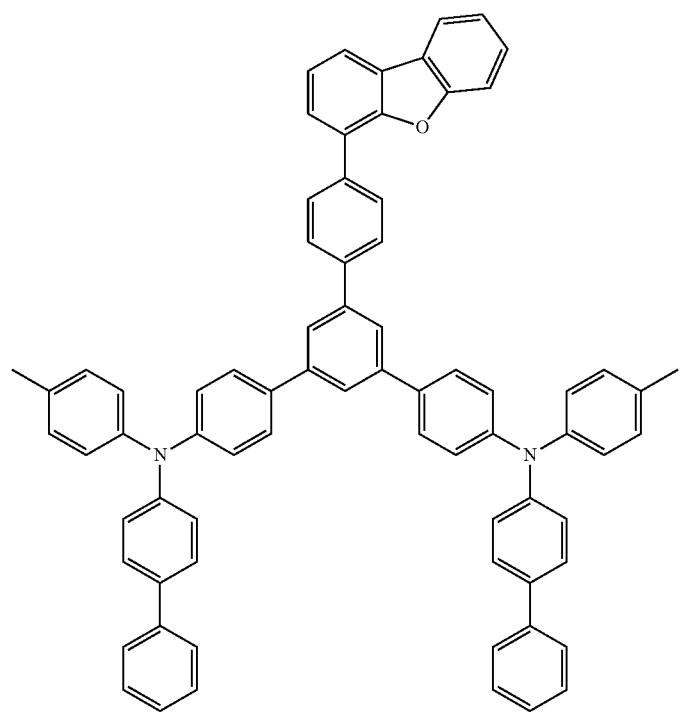

-continued
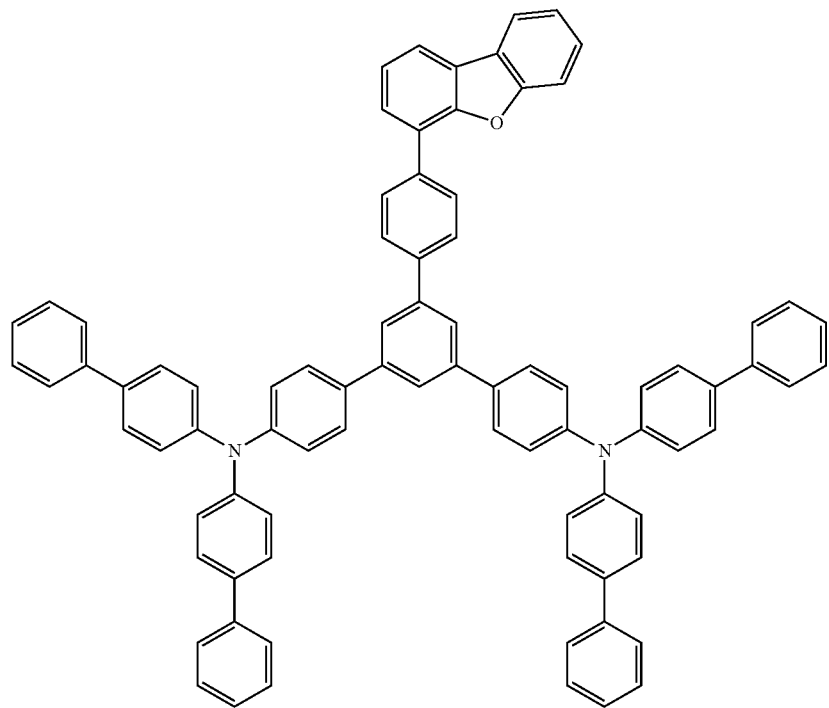
23
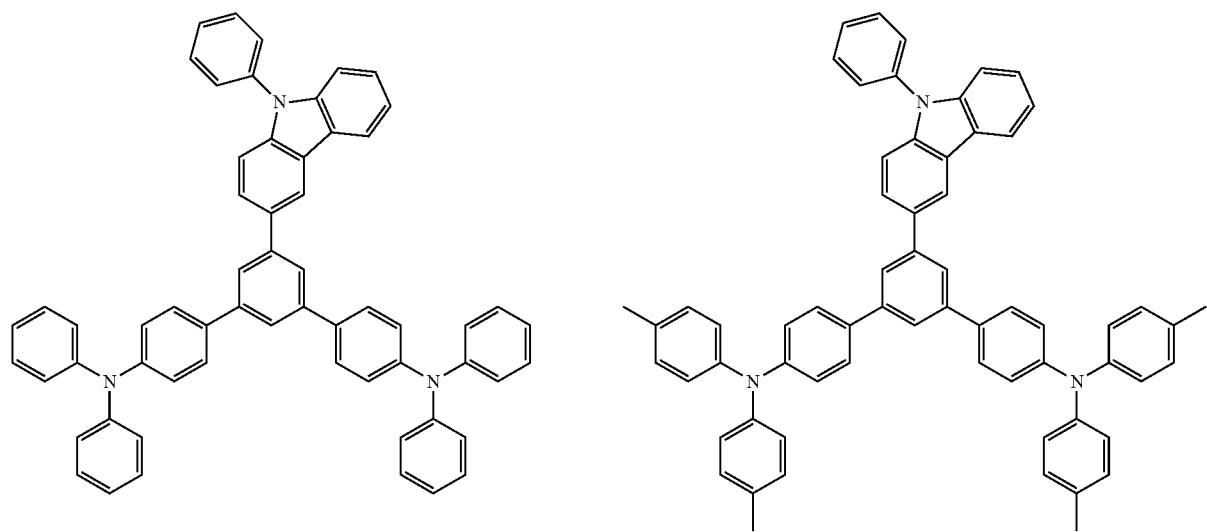
24
25

26
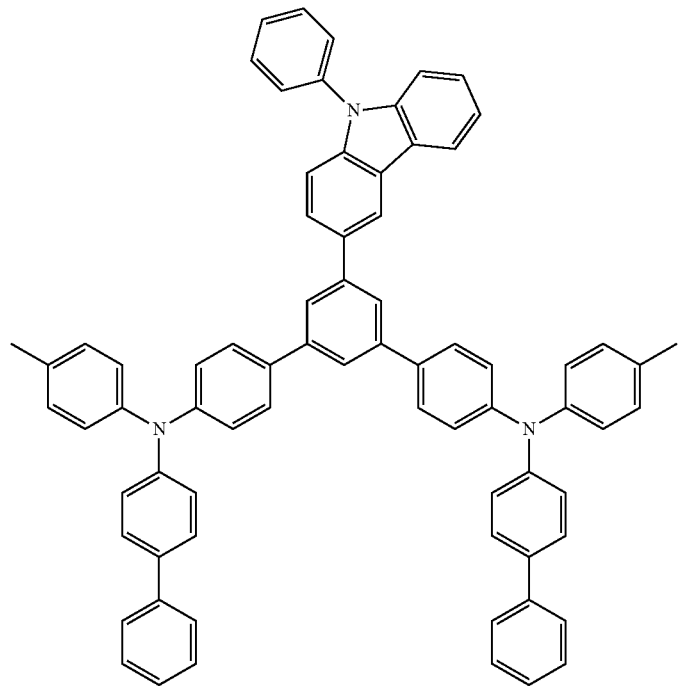
27
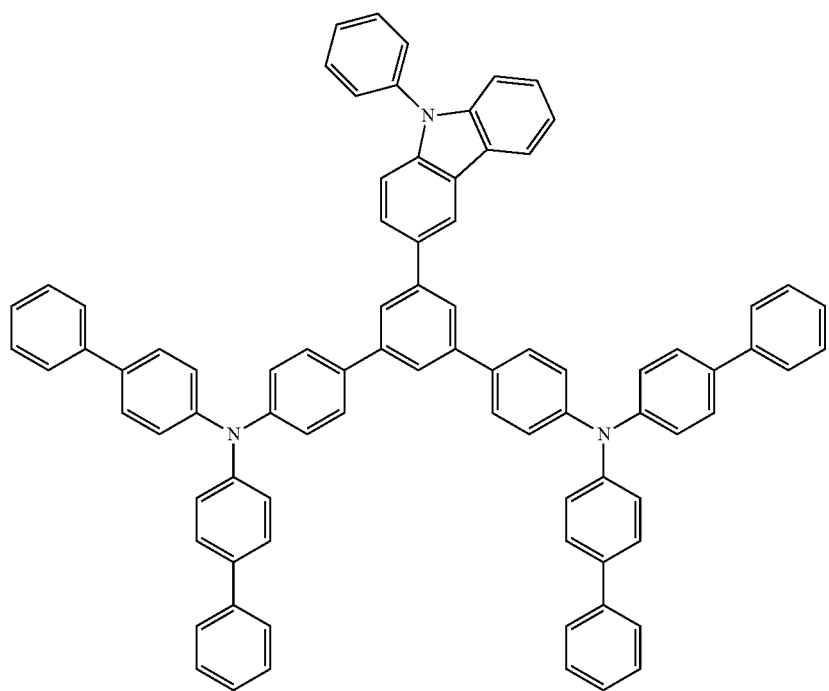

28
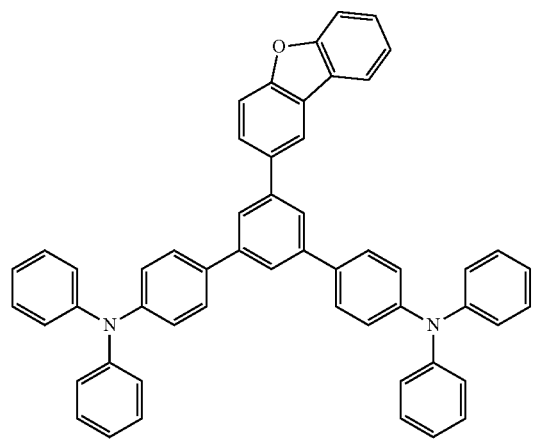
29
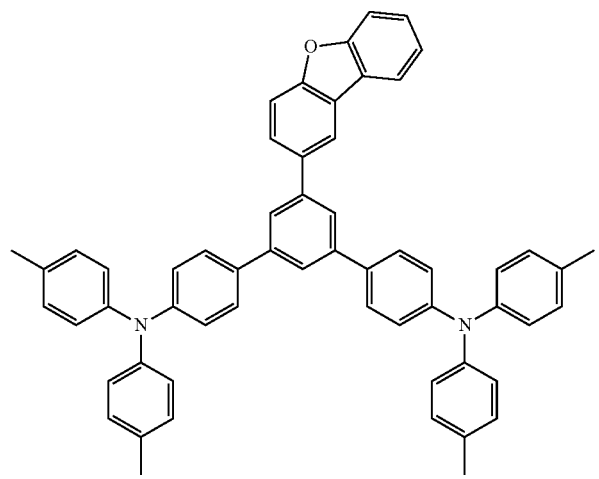
30
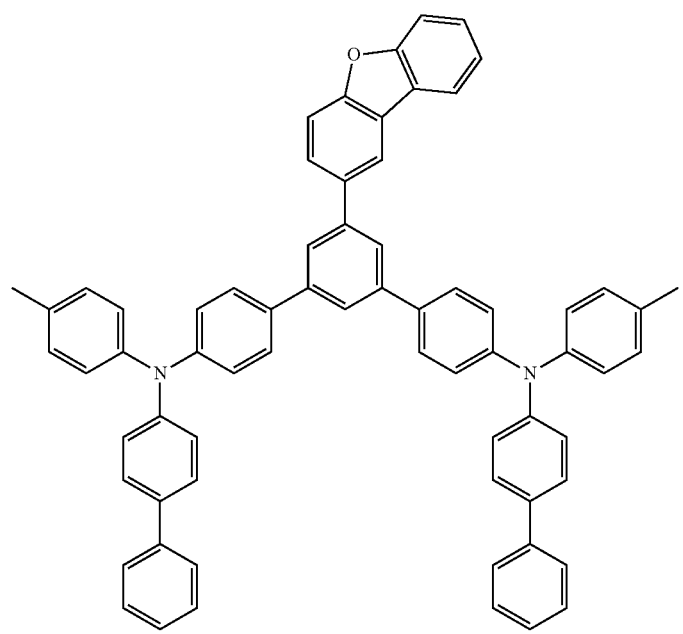

-continued

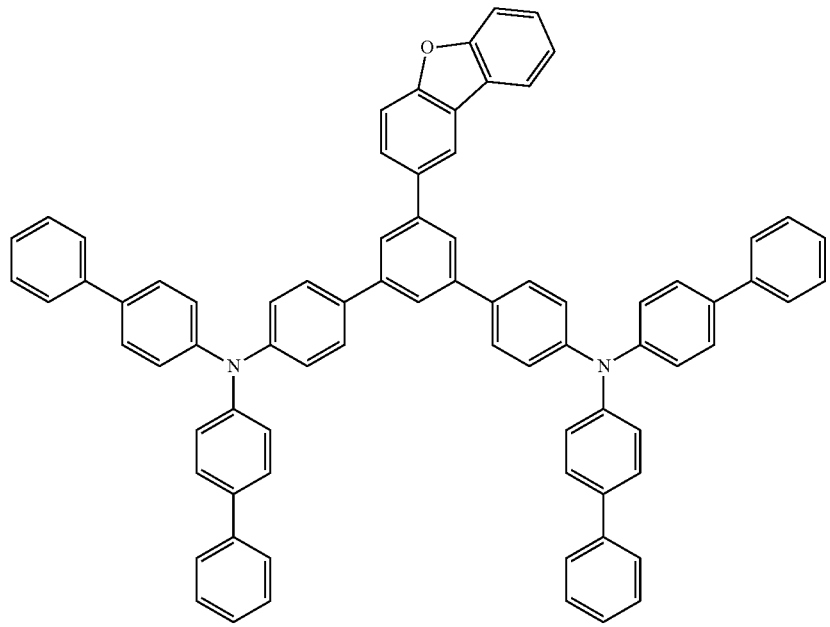

31

According to an embodiment of the present invention, an organic electroluminescent (EL) device including the compound for an organic EL device according to the present invention may be provided.

According to an embodiment of the present invention, an organic EL device may include a first electrode, a second electrode, and a single organic layer or a plurality of organic layers between the first electrode and the second electrode, and one or more organic layers selected from among the single organic layer or the plurality of organic layers may include the compound for an organic EL device according to the present invention.

According to an embodiment of the present invention, the single organic layer or the plurality of organic layers may include a light emitting layer.

According to an embodiment of the present invention, the plurality of organic layers may include a light emitting layer, and the plurality of organic layers may further include one or more selected from among an electron injection layer, an electron transport layer, a hole blocking layer, an electron blocking layer, a hole transport layer and a hole injection layer.

According to an embodiment of the present invention, the light emitting layer may include a host and a dopant.

Advantageous Effects

According to an embodiment of the present invention, a compound including terphenyl group derivatives having a diarylamine group is formed, making it possible to provide a variety of derivatives, whereby the properties of the compound can be adjusted. When this compound is contained in the organic layer of an organic EL device, various properties can be exhibited. Moreover, thermal stability and light emission efficiency of the organic EL device using the compound can be improved, and the use of the compound as a hole transport layer material enables a triplet exciton of a phosphorescent light emitting material to be confined, consequently improving the efficiency of the organic EL device.

DESCRIPTION OF DRAWINGS

The above and other objects, features and advantages of the present invention will be more clearly understood from the following detailed description taken in conjunction with the accompanying drawings, in which:

FIG. 1 is a cross-sectional view illustrating an organic EL device according to an embodiment of the present invention; and FIG. 2 is a cross-sectional view illustrating an organic EL device according to another embodiment of the present invention.

EMBODIMENTS FOR INVENTION

The present invention may be variously modified, and may have a variety of embodiments, and is intended to illustrate specific embodiments. However, the following description does not limit the present invention to specific embodiments, and should be understood to include all variations, equivalents or substitutions within the spirit and scope of the present invention. Furthermore, in the description of the present invention, when it is determined that the detailed description of the related art would obscure the gist of the present invention, the description thereof will be omitted.

Also, in the following description, the terms "first," "second" and the like are used to differentiate a certain component from other components, but the configuration of such components should not be construed to be limited by the terms. For example, a first component may be referred to as a second component, and a second component may be referred to as a first component, within the scope of the present invention.

Also, when any one component is mentioned to be "formed" or "stacked" on another component, it may be directly attached to the entire surface or one surface of another component, or a further component may be additionally interposed therebetween.

Unless otherwise stated, the singular expression includes a plural expression. In this application, the terms "include" and "have" are used to designate the presence of features, numbers, steps, operations, components, parts or combinations thereof described in the specification, not intending to exclude the presence or additional possibility of one or more different features, numbers, steps, operations, components, parts or combinations thereof are not excluded.

As used herein, unless otherwise defined, the term "valence bond" means a single bond, a double bond or a triple bond.

As used herein, unless otherwise defined, the term "substituted" means that at least one hydrogen on a substituent or a compound is substituted with deuterium, a halogen group, a hydroxyl group, an amino group, a C1 to C30 amine group, a nitro group, a silyl group, a C1 to C30 alkyl group, a C1 to C30 alkylsilyl group, a C3 to C30 cycloalkyl group, a C1 to C30 heterocycloalkyl group, a C6 to C30 aryl group, a C1 to C30 heteroaryl group, a C1 to C20 alkoxy group, a C1 to C10 trifluoroalkyl group or a cyano group.

Further, among the halogen group, the hydroxyl group, the amino group, the C1 to C30 amine group, the silyl group, the C1 to C30 alkyl group, the C1 to C30 alkylsilyl group, the C3 to C30 cycloalkyl group, the C6 to C30 aryl group, the C1 to C20 alkoxy group, the C1 to C10 trifluoroalkyl group or the cyano group, which is substituted, two adjacent substituents may be fused to form a ring.

As used herein, unless otherwise defined, the term "hetero" means a functional group containing 1~4 heteroatoms selected from the group consisting of N, O, S and P, the remainder being carbon.

As used herein, unless otherwise defined, the term "combination thereof" means that two or more substituents are coupled with each other by a linker or two or more substituents are condensed to each other.

As used herein, unless otherwise defined, the term "hydrogen" means hydrogen, deuterium or tritium.

As used herein, unless otherwise defined, the term "alkyl group" means an aliphatic hydrocarbon group.

The alkyl group may be a "saturated alkyl group" without any double bond or triple bond.

The alkyl group may be an "unsaturated alkyl group" with at least one double bond or triple bond.

The term "alkenylene group" means a functional group having at least one carbon-carbon double bond between at least two carbon atoms, and the term "alkynylene group" means a functional group having at least one carbon-carbon triple bond between at least two carbon atoms. The alkyl group may be branched, linear or cyclic, regardless of whether it is saturated or unsaturated.

The alkyl group may be a C1 to C30 alkyl group, preferably a C1 to C20 alkyl, more preferably a C1 to C10 alkyl group, and much more preferably a C1 to C6 alkyl group.

For example, a C1 to C4 alkyl group indicates an alkyl chain containing 1~4 carbon atoms, particularly an alkyl chain which is selected from the group consisting of methyl, ethyl, propyl, isopropyl, n-butyl, iso-butyl, sec-butyl and t-butyl.

Specific examples of the alkyl group include a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, etc.

The "amine group" includes an arylamine group, an alkylamine group, an arylalkylamine group, or an alkylarylamine group.

The term "cycloalkyl group" refers to a monocyclic or fused-ring polycyclic (i.e., rings which share adjacent pairs of carbon atoms) functional group.

The term "heterocycloalkyl group" means a cycloalkyl group containing 1~4 heteroatoms selected from the group consisting of N, O, S and P, the remainder being carbon. In the case where the heterocycloalkyl group is a fused ring, at least one ring may contain 1~4 heteroatoms.

The term "aromatic group" means a cyclic functional group where all ring atoms have p-orbitals, and these p-orbitals form conjugation. Specific examples thereof include an aryl group and a heteroaryl group.

The term "aryl group" refers to a monocyclic or fused-ring polycyclic (i.e., rings which share adjacent pairs of carbon atoms) functional group.

The term "heteroaryl group" means an aryl group containing 1~4 heteroatoms selected from the group consisting of N, O, S and P, the remainder being carbon. In the case where the heteroalkyl group is a fused ring, at least one ring may contain 1~4 heteroatoms.

In the aryl group and the heteroaryl group, the number of ring atoms is the sum of the number of carbons and the number of non-carbon atoms.

When alkyl and aryl are used in combination as in "alkylaryl group" or "arylalkyl group," "alkyl" and "aryl" respectively have the meanings as above.

The term "arylalkyl group" means an aryl substituted alkyl radical such as benzyl, and is incorporated in the alkyl group.

The term "alkylaryl group" means an alkyl substituted aryl radical, and is incorporated in the aryl group.

Below is a description of embodiments of the present invention with reference to the appended drawings, wherein the same or similar components are designated by the same reference numerals and the overlapping description thereof is omitted.

With reference to FIGS. 1 and 2, according to an embodiment of the present invention, an organic EL device 1 including the compound for an organic EL device according to the present invention may be provided.

According to another embodiment of the present invention, an organic EL device includes a first electrode 110, a second electrode 150, and a single organic layer or a plurality of organic layers 130 between the first electrode and the second electrode, and one or more organic layers selected from among the single organic layer or the plurality of organic layers 130 may include the compound for an organic EL device according to the present invention.

As such, the single organic layer or the plurality of organic layers 130 may include a light emitting layer 134.

The plurality of organic layers 130 include a light emitting layer 134, and the plurality of organic layers 130 may further include one or more selected from among an electron injection layer 131, an electron transport layer 132, a hole blocking layer 133, an electron blocking layer 135, a hole transport layer 136 and a hole injection layer 137.

The light emitting layer 134 may include a host and a dopant.

The organic EL device is preferably supported by a transparent substrate. The material for the transparent substrate is not particularly limited so long as it has good mechanical strength, thermal stability and transparency. Specific examples thereof may include glass, a transparent plastic film, etc.

The anode material of the organic EL device according to the present invention may include a metal, an alloy, an electrically conductive compound or a mixture thereof, having a work function of 4 eV or more. Specific examples thereof may include Au metal or a transparent conductive material such as CuI, ITO (indium tin oxide), $SnO_2$ and ZnO. The thickness of the anode film is preferably set to 10~200 nm.

The cathode material of the organic EL device according to the present invention may include a metal, an alloy, an electrically conductive compound or a mixture thereof, having a work function of less than 4 eV. Specific examples thereof may include Na, a Na—K alloy, calcium, magnesium, lithium, a lithium alloy, indium, aluminum, a magnesium alloy, or an aluminum alloy. In addition, aluminum/$AlO_2$, aluminum/lithium, magnesium/silver or magnesium/indium may be used. The thickness of the cathode film is preferably set to 10~200 nm.

In order to increase light emission efficiency of the organic EL device, one or more electrodes preferably have a light transmittance of 10% or more. The sheet resistance of the electrodes is preferably hundreds of Q/mm or less. The thickness of the electrodes falls in the range of 10 nm~1 μm, and preferably 10~400 nm. Such electrodes may be manufactured in the form of a thin film using the above electrode material via vapor deposition such as chemical vapor deposition (CVD), physical vapor deposition (PVD) or the like, or sputtering.

When the compound for an organic EL device according to the present invention is used so as to be adapted for the purposes of the present invention, a hole transport material, a hole injection material, a light emitting layer material, a host material for a light emitting layer, an electron transport material, and an electron injection material, which are known, may be used alone in each organic layer, or may be used in selective combination with the compound for an organic EL device according to the present invention.

Examples of the hole transport material may include porphyrin compound derivatives including N,N-dicarbazolyl-3,5-benzene (mCP), poly(3,4-ethylenedioxythiophene):poly(styrenesulfonate) (PEDOT:PSS), N,N'-di(1-naphthyl)-N,N'-diphenylbenzidine (NPD), N,N'-diphenyl-N,N'-di(3-methylphenyl)-4,4'-diaminobiphenyl (TPD), N,N'-diphenyl-N,N'-dinaphthyl-4,4'-diaminobiphenyl, N,N,N',N'-tetra-p-tolyl-4,4'-diaminobiphenyl, N,N,N'N'-tetraphenyl-4,4'-diaminobiphenyl, 1,10,15,20-tetraphenyl-21H,23H-porphyrin copper(II), etc., triarylamine derivatives including polymers having an aromatic tertiary amine in the main chain or side chain thereof, 1,1-bis(4-di-p-tolylaminophenyl)cyclohexane, N,N,N-tri(p-tolyl)amine and 4,4',4'-tris[N-(3-methylphenyl)-N-phenylamino]triphenylamine, carbazole derivatives including N-phenylcarbazole and polyvinylcarbazole, phthalocyanine derivatives including metal-free phthalocyanine and copper phthalocyanine, starburst amine derivatives, enaminestilbene-based derivatives, aromatic tertiary amine-containing styrylamine compound derivatives, polysilane, etc.

Examples of the electron transport material may include diphenylphosphine oxide-4-(triphenylsilyl)phenyl (TSPO1), $Alq_3$, 2,5-diaryl sylol derivatives (PyPySPyPy), perfluorinated compounds (PF-6P), octasubstituted cyclooctatetraene compounds (COTs), etc.

In the organic EL device according to the present invention, an electron injection layer, an electron transport layer, a hole transport layer and a hole injection layer may be provided in the form of a single layer containing one or more kinds of the above compound, or may be provided in the form of a plurality of stacked layers containing different kinds of compounds.

The light emitting material may include, for example, photoluminescent fluorescent materials, fluorescent brighteners, laser dyes, organic scintillators and fluorescence analysis reagents. Specific examples thereof include carbazole-based compounds, phosphine oxide-based compounds, carbazole-based phosphine oxide compounds, polyaromatic compounds including bis((3,5-difluoro-4-cyanophenyl)pyridine)iridium picolinate (FCNIrpic), tris(8-hydroxyquinoline) aluminum ($Alq_3$), anthracene, phenanthrene, pyrene, chrysene, perylene, coronene, rubrene and quinacridone, oligophenylene compounds including quaterphenyl, scintillators for liquid scintillation including 1,4-bis(2-methylstyryl)benzene, 1,4-bis(4-methylstyryl)benzene, 1,4-bis(4-methyl-5-phenyl-2-oxazolyl)benzene, 1,4-bis(5-phenyl-2-oxazolyl)benzene, 2,5-bis(5-t-butyl-2-benzoxazolyl)thiophene, 1,4-diphenyl-1,3-butadiene, 1,6-diphenyl-1,3,5-hexatriene and 1,1,4,4-tetraphenyl-1,3-butadiene, metal complexes of oxine derivatives, coumarine dyes, dicyanomethylenepyran dyes, dicyanomethylenethiopyran dyes, polymethine dyes, oxobenzanthracene dyes, xanthene dyes, carbostyryl dyes, perylene dyes, oxazine compounds, stilbene derivatives, spiro compounds, oxadiazole compounds, etc.

Each layer of the organic EL device according to the present invention may be provided in the form of a thin film using a known process such as vacuum deposition, spin coating or casting, or may be manufactured using each layer material. The thickness of each layer is not particularly limited, but may be appropriately set depending on the material properties, and may be typically determined in the range of 2~5,000 nm.

Because the compound for an organic EL device according to the present invention may be subjected to vacuum deposition, a thin film formation process is simple and a uniform thin film which does not substantially have pin holes may be easily obtained.

A better understanding of the present invention regarding the synthesis of the compound for an organic EL device and the manufacture of the organic EL device including the same may be obtained through the following examples which are set forth to illustrate, but are not to be construed as limiting, the present invention.

EXAMPLE

Preparation Example 1. Synthesis of Intermediate 1

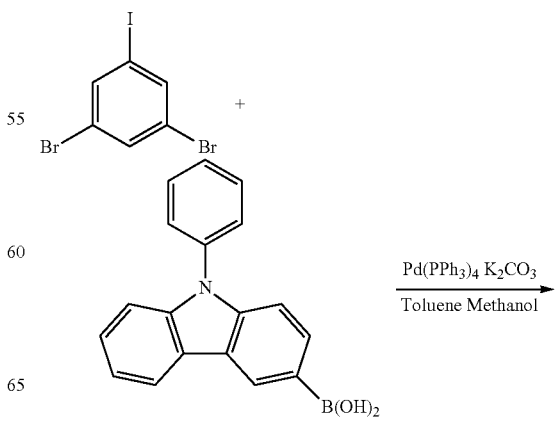

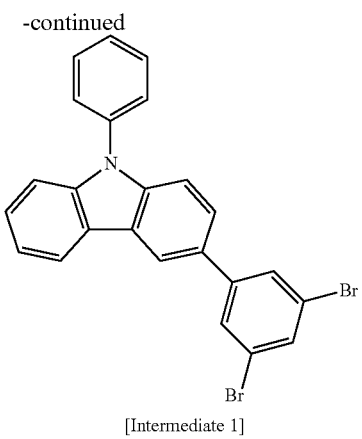

[Intermediate 1]

In a 250 mL round-bottom three-neck flask under a nitrogen atmosphere, 12 g of 1,3-dibromo-5-iodobenzene, 9.5 g of N-phenylcarbazole-3-boronic acid, 1.2 g of tetrakis(triphenylphosphine)palladium(0), 9 g of potassium carbonate, 120 ml of toluene and 30 ml of methanol were placed, and stirred at 80° C. for 6 hrs. The reaction solution was cooled and then extracted with dichloromethane and water, and the extracted solution was concentrated. The solution which was subjected to column chromatography using a solvent mixture of dichloromethane and n-hexane was concentrated, thus obtaining 9.3 g of Intermediate 1 (yield 62%).

$^1$H NMR (CDCl$_3$, 600 MHz) δ 8.28 (s, 1H), 8.20-8.18 (d, 1H), 7.8-7.76 (s, 2H), 7.63-7.62 (m, 3H), 7.58-7.55 (m, 3H), 7.51-7.48 (t, 1H), 7.45-7.40 (m, 3H), 7.34-7.3 (t, 1H)

Preparation Example 2. Synthesis of Intermediate 2

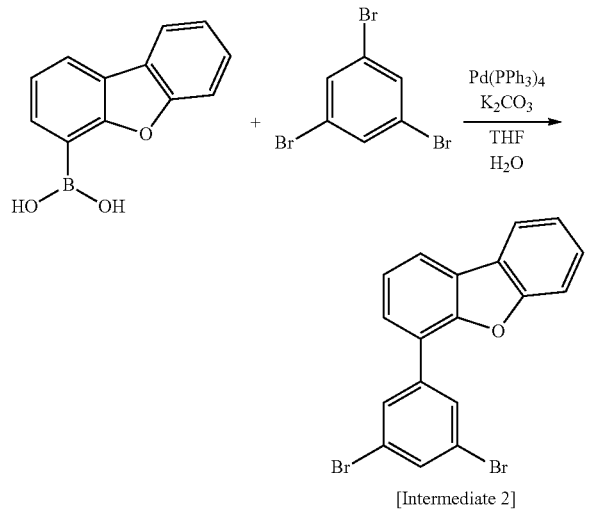

[Intermediate 2]

In a 250 ml round-bottom three-neck flask under a nitrogen atmosphere, 8 g of 1,3,5-tribromobenzene, 5 g of dibenzofuranyl-4-boronic acid, 0.3 g of tetrakis(triphenylphosphine)palladium(0), 9 g of potassium carbonate, 120 ml of tetrahydrofuran and 30 ml of water were placed, and stirred at 60° C. for 6 hrs. The reaction solution was cooled and then extracted with dichloromethane and water, and the extracted solution was concentrated. The solution which was subjected to column chromatography using a solvent mixture of dichloromethane and n-hexane was concentrated, thus obtaining 6.3 g of Intermediate 2 (yield 66%).

$^1$H NMR (CDCl$_3$, 600 MHz) δ 8.01-7.95 (m, 4H), 7.72 (s, 1H), 7.66-7.63 (d, 1H), 7.56-7.53 (d, 1H), 7.52-7.48 (dd, 1H), 7.45-7.42 (dd, 1H), 7.41-7.36 (dd, 1H)

Preparation Example 3. Synthesis of Intermediate 3

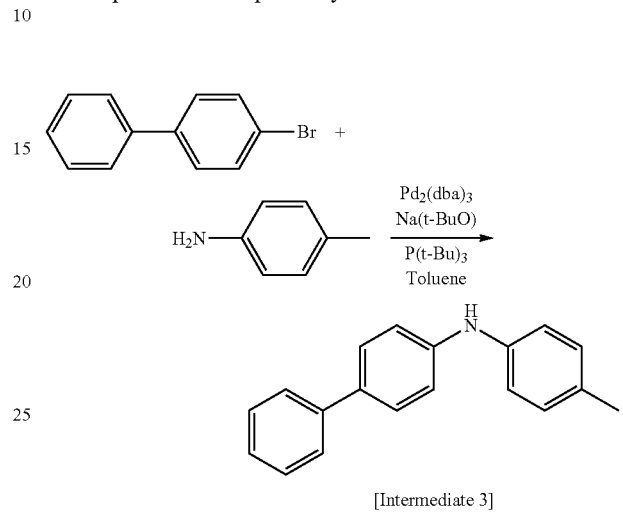

[Intermediate 3]

In a 250 ml round-bottom three-neck flask under a nitrogen atmosphere, 4 g of 4-bromobiphenyl, 3.1 g of p-toluidine, 0.3 g of tris(dibenzylideneacetone)dipalladium(0), 4.2 g of sodium tert-butoxide, 0.1 g of Tri-tert-butylphosphine and 120 ml of toluene were placed, and stirred at 110° C. for 8 hrs. The reaction solution was cooled and then extracted with dichloromethane and water, and the extracted solution was concentrated. The solution which was subjected to column chromatography using a solvent mixture of dichloromethane and n-hexane was concentrated, thus obtaining 4.3 g of Intermediate 3 (yield 97%).

$^1$H NMR (CDCl$_3$, 600 MHz) δ 7.59-7.54 (d, 2H), 7.53-7.46 (d, 2H), 7.43-7.39 (dd, 2H), 7.32-7.27 (t, 1H), 7.15-7.00 (m, 6H), 2.32 (s, 3H)

Preparation Example 4. Synthesis of Intermediate 4

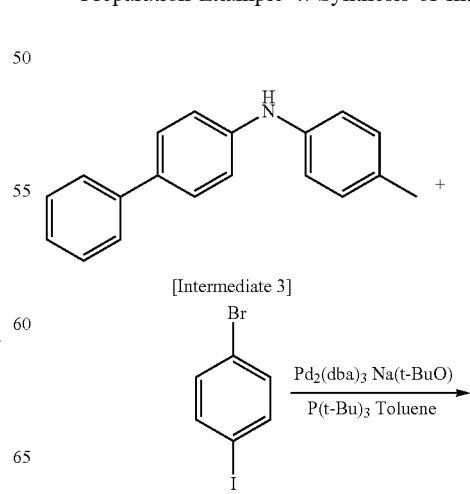

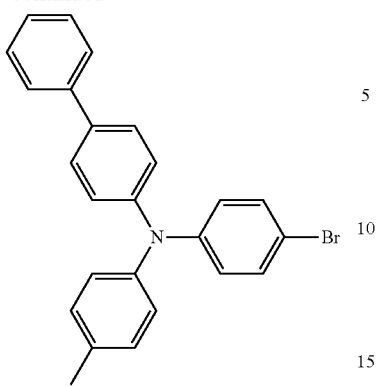

[Intermediate 4]

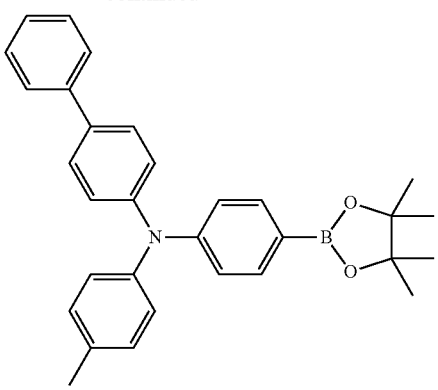

[Intermediate 5]

In a 250 ml round-bottom three-neck flask under a nitrogen atmosphere, 4 g of Intermediate 3 synthesized in Preparation Example 3, 5.2 g of 4-bromo iodobenzene, 0.2 g of tris(dibenzylideneacetone)dipalladium(0), 3.3 g of sodium tert-butoxide, 0.2 g of triphenylphosphine and 60 ml of toluene were placed, and stirred at 110° C. for 8 hrs. The reaction solution was cooled and then extracted with dichloromethane and water, and the extracted solution was concentrated. The solution which was subjected to column chromatography using a solvent mixture of dichloromethane and n-hexane was concentrated, thus obtaining 4.3 g of Intermediate 4 (yield 67%).

$^1$H NMR (CDCl$_3$, 600 MHz) δ 7.60-7.54 (d, 2H), 7.51-7.46 (d, 2H), 7.45-7.39 (dd, 2H), 7.36-7.27 (m, 3H), 7.15-7.00 (m, 6H), 6.99-6.95 (d, 2H), 2.33 (s, 3H)

Preparation Example 5. Synthesis of Intermediate 5

In a 100 ml round-bottom three-neck flask under a nitrogen atmosphere, 4 g of Intermediate 4 synthesized in Preparation Example 4, 4.8 g of bis(pinacolato)diboron, 0.2 g of 1,1'-bis(diphenylphosphino ferrocene)dichloropalladium (II), 2.9 g of potassium acetate and 60 ml of DMSO were placed, and stirred at 110° C. for 8 hrs. The reaction solution was cooled and then extracted with dichloromethane and water, and the extracted solution was concentrated. The solution which was subjected to column chromatography using a solvent mixture of dichloromethane and n-hexane was concentrated, thus obtaining 4.1 g of Intermediate 5 (yield 91%).

$^1$H NMR (CDCl$_3$, 600 MHz) δ 7.70-7.66 (m, 2H), 7.58-7.53 (d, 2H), 7.48-7.43 (m, 2H), 7.42-7.37 (dd, 2H), 7.31-7.27 (t, 1H), 7.16-7.12 (m, 2H), 7.11-7.03 (m, 6H), 2.32 (s, 3H), 1.33 (s, 12H)

Example 1. Synthesis of Compound 6

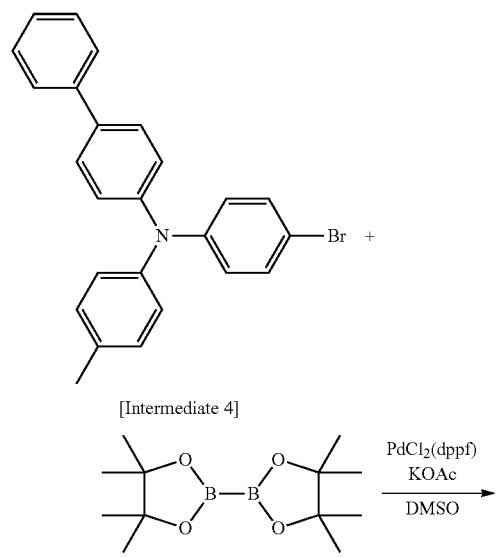

[Intermediate 4]

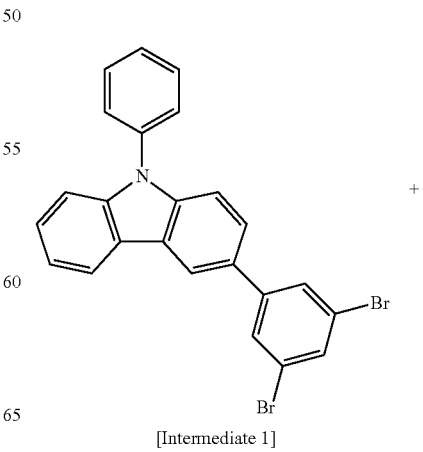

[Intermediate 1]

Example 2. Synthesis of Compound 17

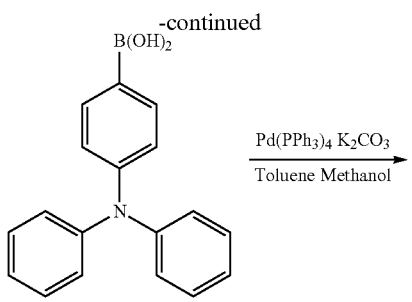

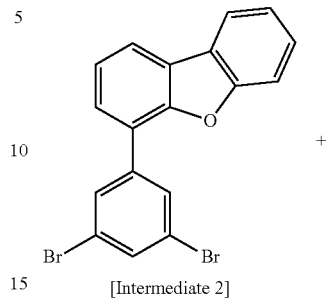

[Intermediate 2]

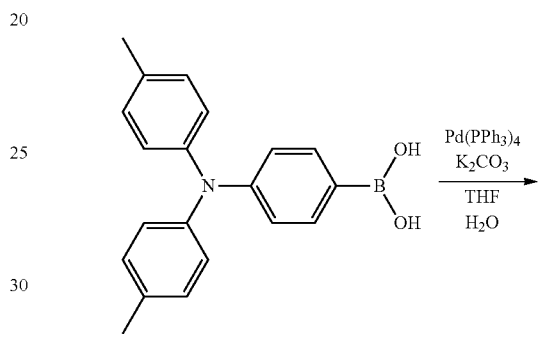

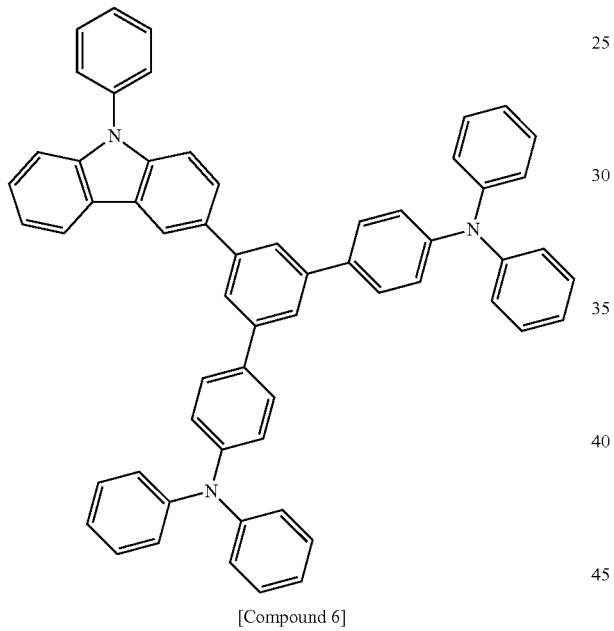

[Compound 6]

In a 100 ml round-bottom three-neck flask under a nitrogen atmosphere, 4 g of Intermediate 1 synthesized in Preparation Example 1, 5.4 g of 4-(diphenylamino)phenylboronic acid, 0.6 g of tetrakis(triphenylphosphine)palladium(0), 4.6 g of potassium carbonate, 50 ml of toluene and 20 ml of methanol were placed, and stirred at 80° C. for 6 hrs. The reaction solution was cooled and then extracted with dichloromethane and water, and the extracted solution was concentrated. The solution which was subjected to column chromatography using a solvent mixture of dichloromethane and n-hexane was concentrated, thus obtaining 2.6 g of Compound 6 (yield 40%).

$^1$H NMR (CDCl$_3$, 600 MHz) δ 8.33 (s, 1H), 8.17-8.16 (d, 1H), 7.8-7.76 (s, 2H), 7.63-7.58 (m, 7H), 7.53 (s, 2H), 7.47-7.44 (t, 1H), 7.42-7.41 (d, 6H), 7.31-7.30 (t, 1H), 7.16 (s, 1H), 7.13-7.12 (d, 2H), 7.07 (s, 2H), 7.04-7.00 (m, 15H), 6.97-6.96 (d, 2H)

LC/Mass [M+H]$^+$: 805.3

[Compound 17]

3.5 g of Compound 17 was obtained in the same manner as in Example 1, with the exception that Intermediate 2 and 4-(ditolyl amino)phenyl boronic acid were used instead of Intermediate 1 and 4-(diphenylamino)phenylboronic acid (yield: 45%).

$^1$H NMR (CDCl$_3$, 600 MHz) δ 8.01-7.98 (m, 3H), 7.98-7.95 (d, 1H), 7.80-7.78 (d, 1H), 7.70-7.68 (d, 1H), 7.62-7.60 (d, 1H), 7.59-7.56 (d, 4H), 7.48-7.43 (m, 2H), 7.38-7.34 (t, 1H), 7.14-7.10 (d, 4H), 7.10-7.04 (m, 16H), 2.32 (s, 12H)

LC/Mass [M+H]$^+$: 786.3

Example 3. Synthesis of Compound 18

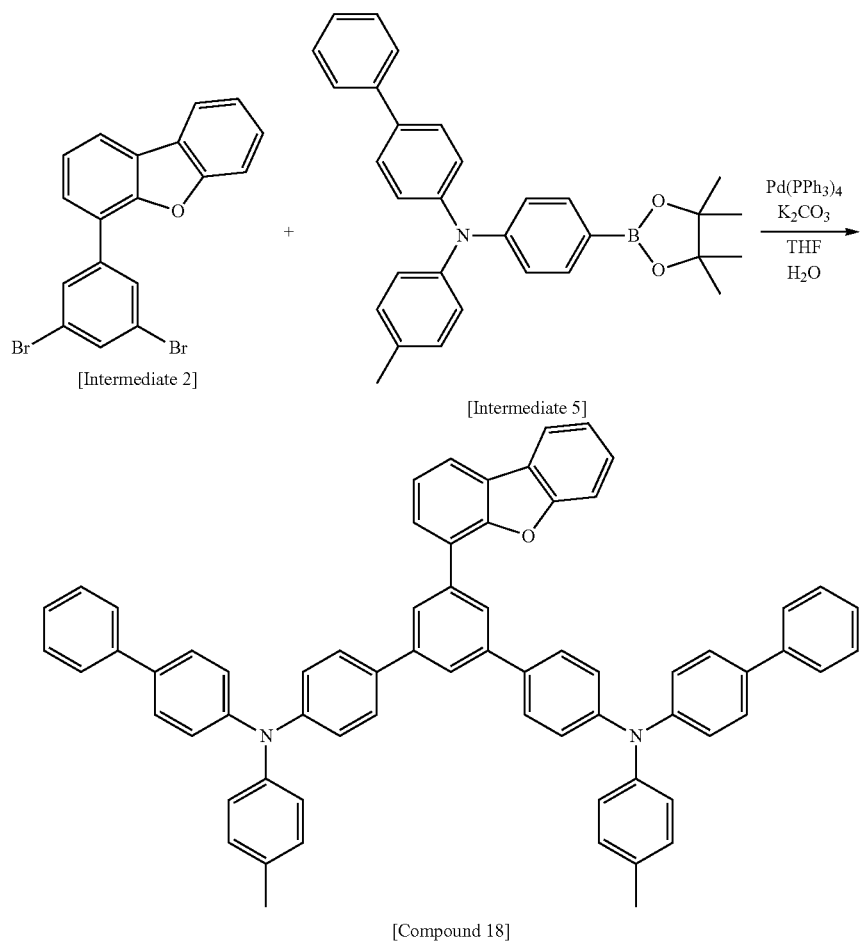

[Compound 18]

5.2 g of Compound 18 was obtained in the same manner as in Example 1, with the exception that Intermediate 2 and Intermediate 5 were used instead of Intermediate 1 and 4-(diphenylamino)phenylboronic acid (Yield: 57%).

$^1$H NMR (CDCl$_3$, 600 MHz) δ 8.05-8.03 (m, 2H), 8.02-7.99 (d, 1H), 7.98-7.96 (d, 1H), 7.83 (s, 1H), 7.72-7.69 (d, 1H), 7.65-7.61 (m, 5H), 7.60-7.56 (d, 4H), 7.51-7.40 (m, 10H), 7.39-7.35 (t, 1H), 7.33-7.29 (t, 2H), 7.23-7.18 (m, 8H), 7.15-7.10 (m, 8H), 2.35 (s, 6H)

LC/Mass [M+H]$^+$: 910.4

Device Example 1. Manufacture of Organic EL Device Including Compound 6 as Second Hole Transport Layer A glass substrate coated with an ITO (indium tin oxide) thin film having a thickness of 100 nm was ultrasonically washed with an isopropyl alcohol solvent, dried, placed in a plasma cleaning system so that the substrate was cleaned using oxygen plasma for 5 min, and then transferred into a vacuum deposition system.

The ITO transparent electrode thus prepared was used as an anode, and DNTPD [N,N'-diphenyl-N,N'-bis-[4-(phenyl-m-tolylamino)-phenyl]-biphenyl-4,4'-diamine] was vacuum deposited on the ITO substrate, thus forming a hole injection layer having a thickness of nm. Subsequently, TBDB [N,N,N',N'-tetra(4-biphenyl)-diaminobiphenylene] was vacuum deposited to a thickness of 30 nm, thus forming a first hole transport layer, and a second hole transport layer was formed to a thickness of 10 nm using compound 6 on the first hole transport layer. GH1 as a host and 6 vol % of GD1 as a dopant were vacuum deposited to a thickness of 30 nm on the hole transport layer, thus forming a light emitting layer.

Thereafter, GH1 as a hole blocking layer were molded to a thickness of 10 nm on the light emitting layer. An electron transport layer was formed to a thickness of 20 nm using Alq$_3$(tris(8-quinolinolato)-aluminium(III)) on the hole blocking layer. 2 nm thick Liq [lithium quinolate] and 100 nm thick Al were sequentially vacuum deposited on the electron transport layer to form a cathode, thereby manufacturing an organic EL device.

Device Example 2. Manufacture of Organic EL Device Including Compound 17 as Second Hole Transport Layer An organic EL device was manufactured in the same manner as in Device Example 1, with the exception that compound 17 as second hole transport layer was used instead of compound 6.

Device Example 3. Manufacture of Organic EL Device Including Compound 18 as Second Hole Transport Layer An organic EL device was manufactured in the same manner as in Device Example 1, with the exception that compound 18 as second hole transport layer was used instead of compound 6.

Comparative Device Example 1

Manufacture of Organic EL Device Including TBDB as Second Hole Transport Layer

An organic EL device was manufactured in the same manner as in Device Example 1, with the exception that TBDB as second hole transport layer was used instead of compound 6.

The chemical formulas of DNTPD, TBDB, GH1, GH2, GD1 and Alq$_3$ used in the Device Example and Comparative Device Example are represented below.

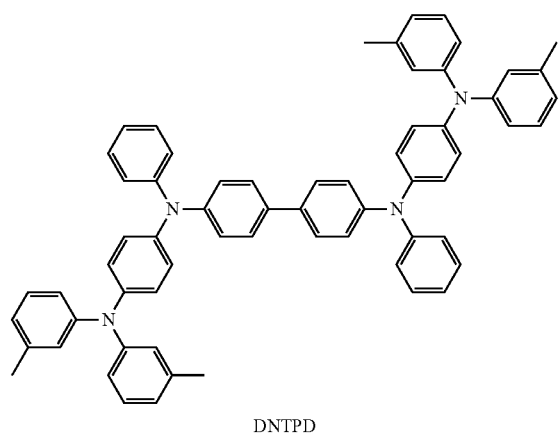

DNTPD

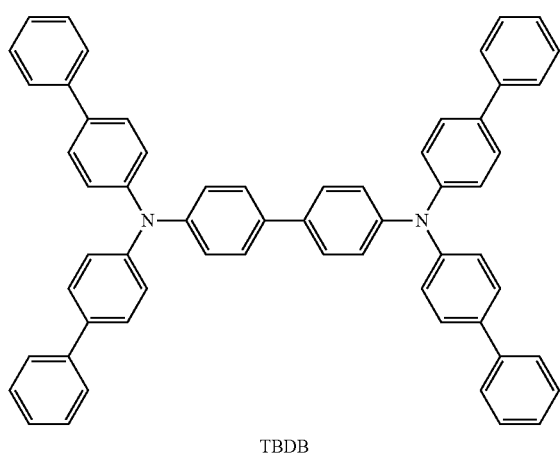

TBDB

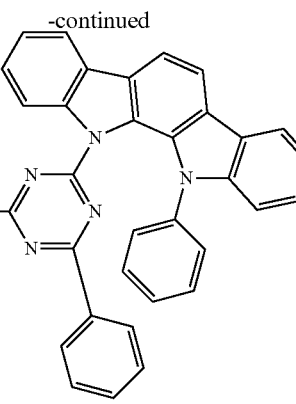

GH1

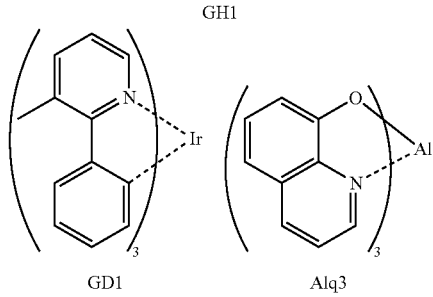

GD1    Alq3

Test Example: Evaluation of Properties of Organic EL Device

The properties of the devices of Device Examples 1 to 3 and Comparative Device Examples 1 were evaluated at a brightness of 1000 cd/m$^2$. The results are shown in Tables 1 below.

Current Density

In the manufactured organic EL devices, while a voltage was increased from 0 V to 10 V, current of each unit device was measured using a current-voltage meter (Keithley 2635A Source Meter), and the measured current value was divided by the area, thus obtaining current density.

Brightness Efficiency

In the manufactured organic EL devices, while a voltage was increased from 0 V to 10 V, the brightness was measured using a brightness meter (Minolta CS-2000), and the measured brightness value was divided by the current value, thus obtaining brightness efficiency.

Color Coordinates

The color coordinates were measured using a brightness meter (Minolta CS-2000).

TABLE 1

|  | 2$^{nd}$ Hole transport layer material | Current density (mA/cm$^2$) | Brightness efficiency (cd/A) | Color coordinates CIE (x, y) |
| --- | --- | --- | --- | --- |
| Device Ex. 1 | Compound 6 | 3.50 | 30.9 | 0.33, 0.62 |
| Device Ex. 2 | Compound 17 | 3.27 | 33.1 | 0.33, 0.62 |
| Device Ex. 3 | Compound 18 | 3.40 | 31.8 | 0.33, 0.61 |
| Comp. Device Ex. 1 | TBDB | 3.57 | 30.3 | 0.33, 0.62 |

According to Table 1, as is apparent from the results of manufacturing organic EL devices using the compounds 6, 17 and 18 according to the present invention as the material for the second hole transport layer, all of the devices exhibited superior properties decreasing Current density and increasing Brightness efficiency compared to when using TBDB as a conventional material.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A compound for an organic electroluminescent device, represented by Chemical Formula 1 below:

[Chemical Formula 1]

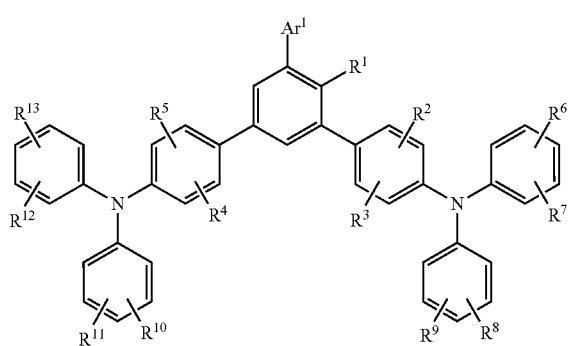

wherein $Ar^1$ is a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or AO is further coupled with a carbon atom adjacent to a carbon atom linked therewith to form a substituted or unsubstituted fused C3 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, $R^1$ is a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or $R^1$ is coupled with $Ar^1$ to form a substituted or unsubstituted fused C1 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, and $R^2$ to $R^{13}$ are identical to or different from each other, and $R^2$ to $R^{13}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or at least one of $R^2$ to $R^{13}$ is further coupled with a carbon atom adjacent to a carbon atom linked therewith to form a substituted or unsubstituted fused C3 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group.

2. The compound of claim 1, which is represented by Chemical Formula 2 below:

[Chemical Formula 2]

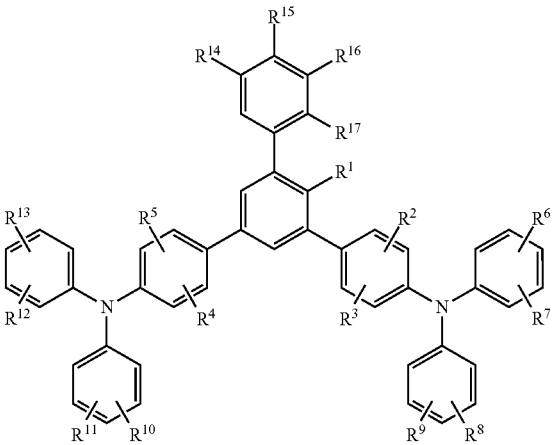

wherein $R^2$ to $R^{16}$ are identical to or different from each other, and $R^2$ to $R^{16}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or at least one of $R^2$ to $R^{16}$ is further coupled with a carbon atom adjacent to a carbon atom linked therewith to form a substituted or unsubstituted fused C3 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, and $R^1$ and $R^{17}$ are identical to or different from each other, and $R^1$ and $R^{17}$ are each independently a hydrogen atom, a substituted or unsubstituted C1 to C30 alkyl group, a substituted or unsubstituted C3 to C30 cycloalkyl group, a substituted or unsubstituted C1 to C30 heterocycloalkyl group, a substituted or unsubstituted C6 to C30 aryl group, or a substituted or unsubstituted C1 to C30 heteroaryl group, or $R^1$ and $R^{17}$, respectively, are linked to form a substituted or unsubstituted fused C1 to C30 cycloalkyl group, a substituted or unsubstituted fused C1 to C30 heterocycloalkyl group, a substituted or unsubstituted fused C6 to C30 aryl group, or a substituted or unsubstituted fused C1 to C30 heteroaryl group, together with 4 carbons atom therebetween, wherein 10 is not a hydrogen atom.

3. The compound of claim 1, which is anyone selected from among compounds 1-2 and 8-15 represented by the following chemical formulas:

1
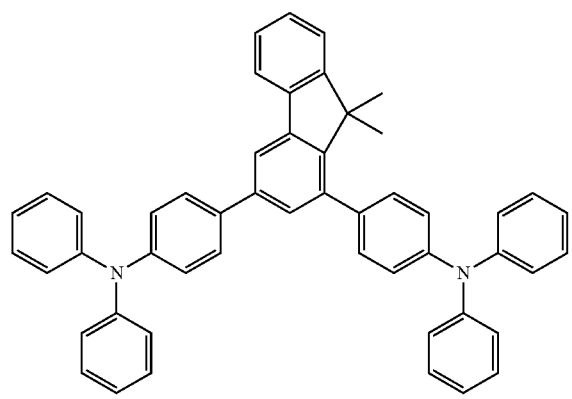
2
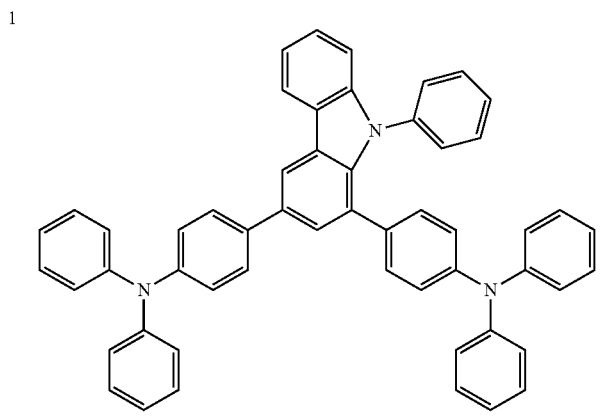
8
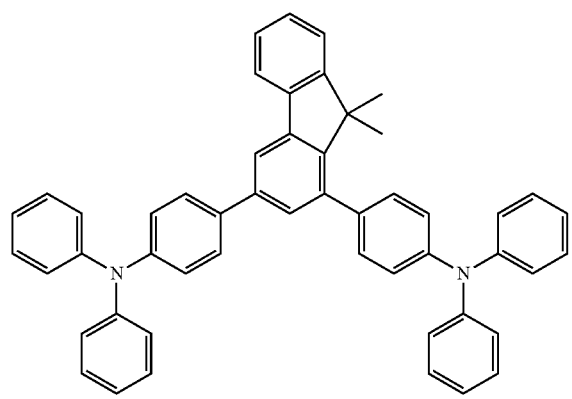
9
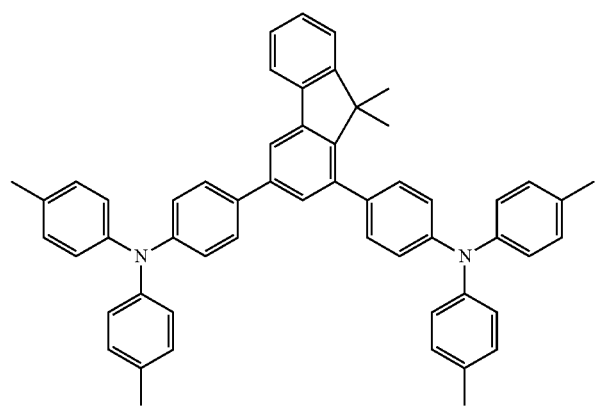
10
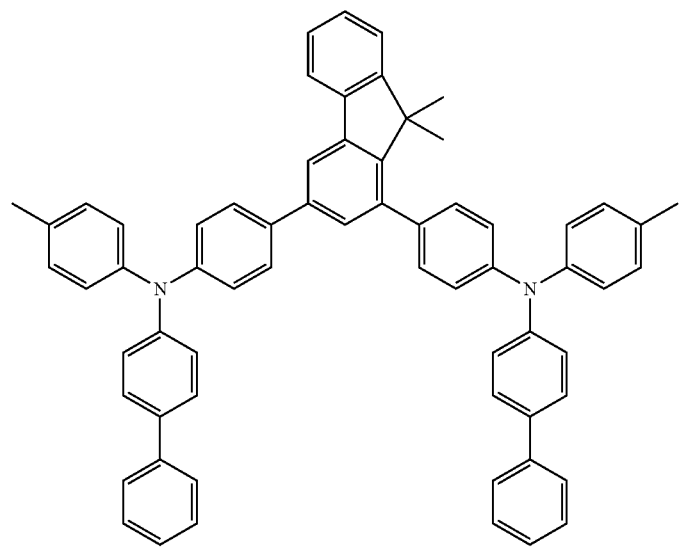

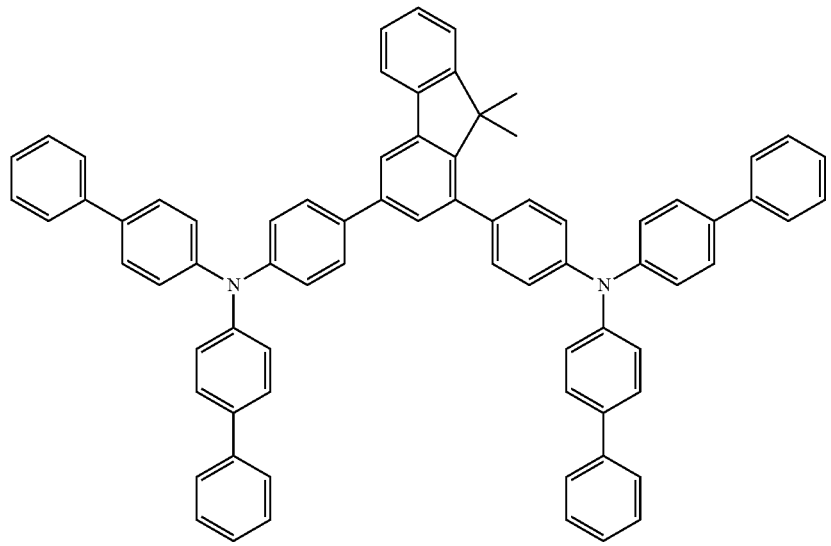
11
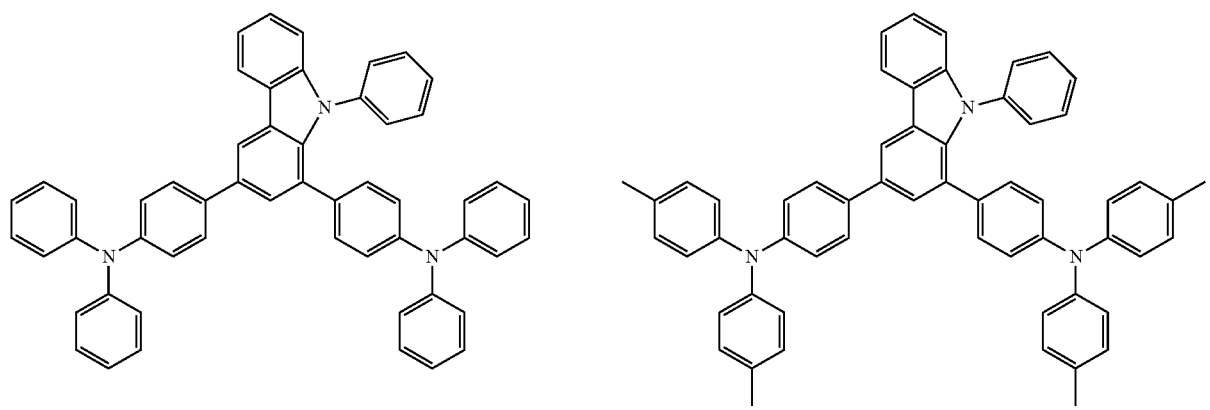
12
13
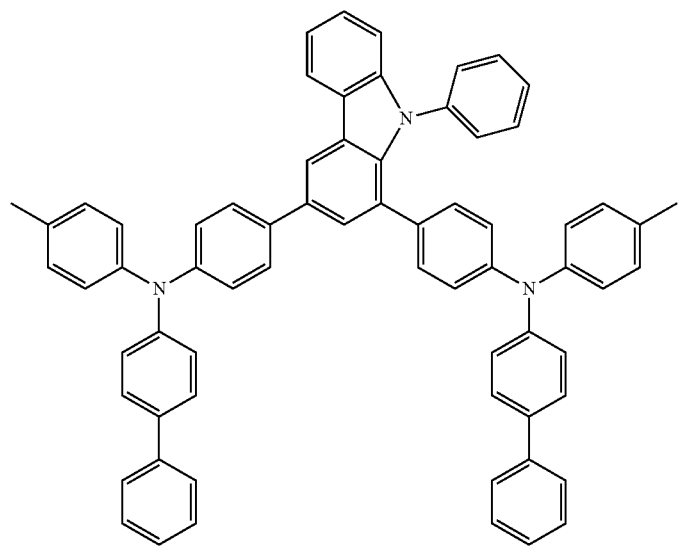
14

-continued

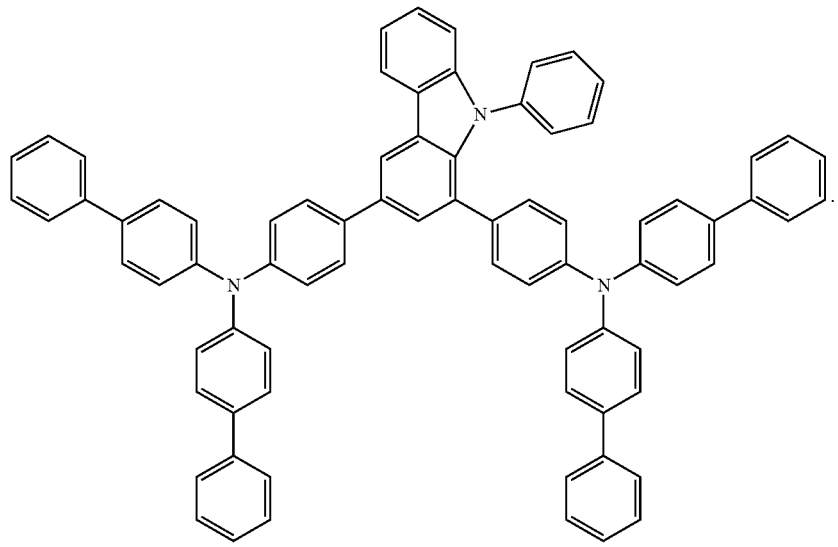
15

4. An organic electroluminescent device, including the compound of claim 1.

5. An organic electroluminescent device, comprising a first electrode, a second electrode, and a single organic layer or a plurality of organic layers between the first electrode and the second electrode, wherein one or more organic layers selected from 10 among the single organic layer or the plurality of organic layers include the compound of claim 1.

6. The organic electroluminescent device of claim 5, wherein the single organic layer or the plurality of organic layers include a light emitting layer.

7. The organic electroluminescent device of claim 5, wherein the plurality of organic layers includes a light emitting layer, and the plurality of organic layers further include one or more elected from among an electron injection layer, an electron transport layer, a hole blocking layer, an electron blocking layer, a hole transport layer and a hole injection layer.

8. The organic electroluminescent device of claim 6, wherein the light emitting layer includes a host and a dopant.

* * * * *